United States Patent
Okazaki

(10) Patent No.: US 8,268,626 B2
(45) Date of Patent: Sep. 18, 2012

(54) METHOD FOR ANALYZING OF LIPOPROTEINS

(76) Inventor: Mitsuyo Okazaki, Chiba (JP)

( * ) Notice: Subject to any disclaimer, the term of this patent is extended or adjusted under 35 U.S.C. 154(b) by 1127 days.

(21) Appl. No.: 11/791,327

(22) PCT Filed: Nov. 24, 2005

(86) PCT No.: PCT/JP2005/022048
§ 371 (c)(1), (2), (4) Date: May 23, 2007

(87) PCT Pub. No.: WO2006/057440
PCT Pub. Date: Jun. 1, 2006

(65) Prior Publication Data
US 2008/0121025 A1 May 29, 2008

Related U.S. Application Data

(60) Provisional application No. 60/630,216, filed on Nov. 24, 2004.

(30) Foreign Application Priority Data

Mar. 31, 2005 (WO) .................. PCT/JP2005/006829

(51) Int. Cl.
*G01N 30/86* (2006.01)
*G01N 30/00* (2006.01)
(52) U.S. Cl. ....... 436/71; 73/61.52; 73/61.43; 73/61.41; 73/53.01
(58) Field of Classification Search .................... 436/71; 73/61.52, 61.43, 61.41, 53.01
See application file for complete search history.

(56) References Cited

U.S. PATENT DOCUMENTS

| 5,417,863 | A | 5/1995 | Varady et al. |
| 2006/0194326 | A1 | 8/2006 | Usui et al. |

FOREIGN PATENT DOCUMENTS

| EP | 1607740 A1 | 12/2005 |
| JP | 8320313 | 12/1996 |
| JP | 9-15225 A | 1/1997 |
| JP | 2002-139501 A | 5/2002 |
| WO | WO-2004/070379 A1 | 8/2004 |

OTHER PUBLICATIONS

Okazaki M., Analysis of lipoprotein subclass in test sample, involves extracting lipoprotein from test samples and determining metabolism movement by chromatography and assaying using lipoprotein profile (English Machine Translation), JP 2002-139501 (submitted on the IDS May 23, 2007).*

(Continued)

*Primary Examiner* — Christine T Mui
(74) *Attorney, Agent, or Firm* — Birch, Stewart, Kolasch & Birch, LLP

(57) ABSTRACT

A method of analysis of lipoproteins according to the present invention comprises the steps of: separating a plurality of classes of lipoproteins contained in a subject sample by liquid chromatography and then detecting signals derived from components included in the separated lipoproteins; and assuming that the lipoproteins are constituted of subclasses estimated from component peaks comprising anchor peaks and extra essential peaks and then calculating an approximated curve corresponding to summation of the component peaks using the above described detected signals.

13 Claims, 21 Drawing Sheets

OTHER PUBLICATIONS

Rifai et al., 'Handbook of Lipoprotein Testing,' 2000, American Association for Clinical Chemistry, Inc., Second Edition, pp. 647-669.*

Hara and Okazaki, High-Performance liquid chromatography of serum lipoproteins, 1986, Methods in Enzymology, vol. 129: 57-78.*

Matsubara, "Usefulness of lipoprotein cholesterol in serum by high performance liquid chromatography," Japanese Journal of Meical Technology, vol. 46, No. 6, 1997, pp. 1005-1009.

Okazaki et al., "Serum Lipoprotein Subclasses by an HPLC Method," The Fats of Life, AACC Lipids and Lipoproteins Division Newsletter, vol. XIV, No. 2, Spring 2000, pp. 1-20.

Usui et al., "A new on-line dual enzymatic method for simultaneous quantification of cholesterol and triglycerides in lipoproteins by HPLC," Journal of Lipid Research, vol. 43, 2002, pp. 805-814.

Matsubara, Japanese Journal of Medical Technology, vol. 46, No. 6, 1997, pp. 1005-1009.

Office Action from Canadian Patent Application No. 2,588,693 dated Jun. 4, 2009.

Okazaki M. et al., "High-performance liquid chromatography of human serum lipoproteins. Selective detection of choline-containing phospholipids by enzymatic reaction", Journal of Chromatography, vol. 231, No. 1, pp. 13-23, 1982. XP009121468.

Okazaki M. et al., "Quantitation method for choline-containing phospholipids in human serum lipoproteins by high performance liquid chromatography", Journal of Biochemistry, vol. 91, No. 4, pp. 1381-1389, 1982. XP009121502.

Extended European Search Report mailed Aug. 26, 2009 for corresponding European Patent Application No. 05811455.4.

Rifai et al., "Handbook of Lipoprotein Testing," Second Edition, pp. 647-669., Mar. 1, 2001.

* cited by examiner

METHOD FOR ANALYZING OF LIPOPROTEINS

This application is the National Phase of PCT/JP2005/022048 filed on Nov. 24, 2005, which designated the United States. This Nonprovisional application claims priority under 35 U.S.C. §119(e) on U.S. Provisional Application No(s). 60/630,216 filed on Nov. 24, 2004 and under 35 U.S.C. §119(a) on Patent Application No(s). PCT/JP2005/006829 filed in Japan on Mar. 31, 2005, the entire contents of which are hereby incorporated by reference.

TECHNICAL FIELD

The present invention relates to a method for analyzing lipoproteins making possible to conduct a data analysis effective for diagnosing various diseases, by fractionating lipoprotein particles being contained in a sample into respective subclasses.

BACKGROUND ART

A JP Patent Publication (Kokai) No. 9-15225 A (1997) discloses a method for classifying lipoprotein particles contained in a subject sample according to the particle size by means of gel filtration liquid chromatography and then for quantifying cholesterol or triglycerides being contained in the classified lipoproteins, wherein the lipoprotein particles are fractionated into chylomicrons, very low density lipoproteins, low density lipoproteins, and high density lipoproteins by subjecting the obtained chromatogram to data processing such as a Gaussian distribution approximation.

A JP Patent Publication (Kokai) No. 2002-139501 A discloses a method for classifying lipoproteins contained in a subject sample according to the particle size by means of gel filtration liquid chromatography and then for quantifying cholesterol or t triglycerides being contained in the classified lipoproteins, wherein the lipoprotein particles are classified into 20 subclasses.

However, the classifying method disclosed in the Patent Document 2 has been applied only to a case where a specific column is used, and respective peak positions for the 20 subclasses (i.e. particle size) have not been supported with theoretical foundation. For example, a particle size of LDL (low density lipoproteins) is determined to be 25.5 nm as a cutoff value when a GGE method (polyacrylamide density gradient gel electrophoresis) is used, and is determined to be about 20 nm based on a size observed by an electron microscope when a NMR method is used, and is determined to be 25.5 nm based on a size obtained by a GGE method when a gel filtration FPLC method is used, and is also determined to be 25.5 nm based on a latex bead or globular proteins when a gel filtration HPLC is used. The particle size may vary depending on ways of estimation when a light scattering method is used. In addition, this particle size may become a different value by determining a molecular weight in accordance with equilibrium ultracentrifugation. Therefore, definition of the lipoprotein subclasses based on the particle size and comparison of respective lipoproteins contained in a subject sample between these subclasses will lead to confusion.

DISCLOSURE OF THE INVENTION

In view of the above described situation, the inventors have made it possible to perform a comparison between the subclasses of a plurality of samples based on a peak position observed in a metabolic disorder patient whose lipoprotein metabolism suggests that the size ranges of VLDL, LDL, and HDL are narrow, even if different gel filtration columns having different specifications of separation and molecular size range are used.

A method for analyzing lipoproteins according to the present invention comprises: a step of separating a plurality of classes of lipoproteins contained in a subject sample by liquid chromatography and then detecting signals derived from components included in the separated lipoprotein particles; and a step of assuming that the lipoproteins are constituted of subclasses estimated from component peaks comprising anchor peaks and extra essential peaks and then calculating an approximated curve corresponding to summation of the component peaks using the detected signals described above.

In addition, examples of the components included in the separated lipoprotein particles include cholesterol, triglycerides, free cholesterol, phospholipids, apolipoproteins and the like. In method for analyzing lipoproteins according to the present invention, the approximated curve may be calculated based on the detected signals derived from at least one component, such as cholesterol, triglycerides, free cholesterol, phospholipids, apolipoproteins and the like.

The anchor peak is a peak whose position is determined experimentally. On the other hand, the extra essential peak is a peak whose position and width are mathematically determined. Assuming that a distribution width of the subclass of LDL is almost the same as that of HDL, and then a position and a width of the extra essential peak are determined so as to be located between the anchor peaks at almost equal intervals.

The number of component peaks may be, but not specifically limited to, 13 to 20. For example, when a TSKgel LipopropakXL column capable of separating a wide range of lipoproteins (those from CM to HDL are separable) is used as a column for the liquid chromatography, 20 component peaks can be established at the maximum. In the case of using a Superose 6HR 10/30 column produced by Pharmacia (or Amersham Biosciences) or a SkylightPak-LDL column produced by Skylight Biotech Inc. whose fractionation range covers from VLDL to BDL (CM is not covered), component peaks whose number is less than 20 can be established. In addition, when a TSK G3000SWXL column is used for example, at least 13 component peaks can be established in order to analysis of LDL and HDL subclasses.

An elution time for the anchor peak (particle size) can be defined as an average elution time of VLDL-sized, LDL-sized, and HDL-sized particles in a profile obtained by using the above described samples derived from a population of mormolipidemic middle-aged men. An elution time for the anchor peak (particle size) can also be defined as an average elution position of VLDL-sized, LDL-sized, and BDL-sized particles in a profile obtained by using the above described samples derived from a case in which lipoprotein lipase activity is absent or little. In addition, an elution time for the anchor peak (particle size) can be defined as an average elution position of BDL-sized particles in a profile obtained by using the above described samples derived from a cholesterol ester transfer protein deficiency. Further, an elution time for the anchor peak (particle size) can also be defined as an average elution position of VLDL-sized particles in a profile obtained by using the above described samples derived from type III hyperlipidemia with ApoE2/2.

The component peaks that have been defined based on a detected signals derived from cholesterol, may be used for calculating the approximated curve regarding a profile derived from cholesterol as well as other approximated curves regarding a profile derived from components other than cholesterol, such as triglycerides, free cholesterol, phospholipids, apolipoproteins and the like.

A method for diagnosing diseases caused by accumulation of visceral fat according to the present invention comprises: a step of preparing a subject sample collected from a subject to be diagnosed, a step of separating a plurality of classes of lipoproteins contained in the above described sample by liquid chromatography; a step of detecting signals derived from components included in the separated lipoprotein particles; a step of assuming that the lipoproteins are constituted of subclasses estimated from component peaks comprising anchor peaks and extra essential peaks, and then calculating an approximated curve corresponding to summation of the component peaks using the detected signals described above; and a step of analyzing said calculated approximated curve.

Examples of diseases caused by the accumulation of visceral fat include arteriosclerotic diseases represented by an ischemic heart disease, for example. That is, as a result of over-nutrition or low physical activity associated with recent changes in life-style which leads to fat accumulation and obesity, the incidence of arteriosclerotic diseases represented by an ischemic heart disease have been increased due to the accumulation of numerous risk factors. This kind of disease is developed by inducing an insulin resistance due to a hereditary predisposition causing the insulin resistance combined with an acquired factor such as obesity. It is important to consider intra-abdominal visceral fat accumulation as a principal upstream cause. The intra-abdominal accumulation of visceral fat caused by obese people as well as by not-obese people closely contributes to the onset of diabetes, hypertension, and coronary artery disease (CAD). Thus, examples of diseases caused by the accumulation of visceral fat include diabetes, hypertension, hyperlipidemia, and coronary artery disease.

In a method for diagnosing diseases caused by accumulation of visceral fat according to the present invention, for example, the visceral fat area is proportionally related to a cholesterol content in a large, medium, or small subclass of VLDL and to a medium, small, or minimum subclass of LDL, while the visceral fat area is inversely related to a cholesterol content in a large or medium subclass of HDL. In other words, a disease due to the accumulation of visceral fat is diagnosed by an increase in a cholesterol content within a large, medium, or small subclass of VLDL and within a medium, small, or very small subclass of LDL, and by a decrease in a cholesterol content within a large or medium subclass of HDL.

A high level of LDL cholesterol is one of the important risk factors. When a concentration of the LDL cholesterol is normal (LDL-C<130 mg/dL), a concentration of cholesterol in the small and very small LDL subclasses are proportionally related to the visceral fat area, while a concentration of cholesterol in the large LDL subclass is inversely related to the visceral fat area. This means that an antiatherogenetic LDL subclass is included in the LDL and that the large LDL subclass acts so as to inhibit the onset of arterial sclerosis. Although a component peak of the large LDL subclass is determined to be an extra essential peak and also determined as a transition component between VLDL and LDL, the component peak can be newly estimated as a new subclass having a clinical meaning according to the present invention. In other words, the onset of arterial sclerosis due to the visceral fat accumulation can be diagnosed by cholesterol content at a component peak of the large LDL subclass.

In addition, it is observed in the coronary artery disease that a cholesterol concentration of the small VLDL subclass increases, a cholesterol concentrations of the small and very small LDL subclass also increase, and a cholesterol concentration of the large HDL subclass decreases, so that it is possible to diagnose the coronary artery disease by measuring cholesterol concentrations in the small VLDL, small and very small LDL, and large HDL subclasses.

In the method for diagnosing coronary artery disease according to the present invention, the step of analyzing lipoprotein contained in a subject sample taken from a subject to be diagnosed using the method for analyzing lipoproteins according to the present invention; and calculating a value according to any one formula selected from (I) to (V):

$$Vs+Ls-Hs; \qquad (I)$$

$$Vs+Ls; \qquad (II)$$

$$Ls; \qquad (III)$$

$$(Vs+Ls)/Hs; \text{ and} \qquad (IV)$$

$$Ls/Hs, \qquad (V)$$

wherein: "Vs" represents the cholesterol content in small VLDL; "Ls" represents the sum of cholesterol contents in small LDL and very small LDL; and "Hs" represents the cholesterol content in large ADL.

In the method for diagnosing coronary artery disease according to the present invention, the step of analyzing further preferably comprises a step of comparing the calculated value with the reference value.

A component peak of the small VLDL subclass being significantly increased in the coronary artery disease is an anchor peak which is determined from a VLDL size derived from the type III hyperlipidemia with Apo E2/2, and thus corresponds to a remnant being increased in the type III hyperlipidemia with Apo E2/2, so that it is recognized that the remnant which is also an important risk factor for the coronary artery can be estimated from a component peak corresponding to small VLDL subclass in the present program.

BEST MODE FOR CARRYING OUT THE INVENTION

The present invention will now be described in detail with reference to the drawings.

Figure 1:
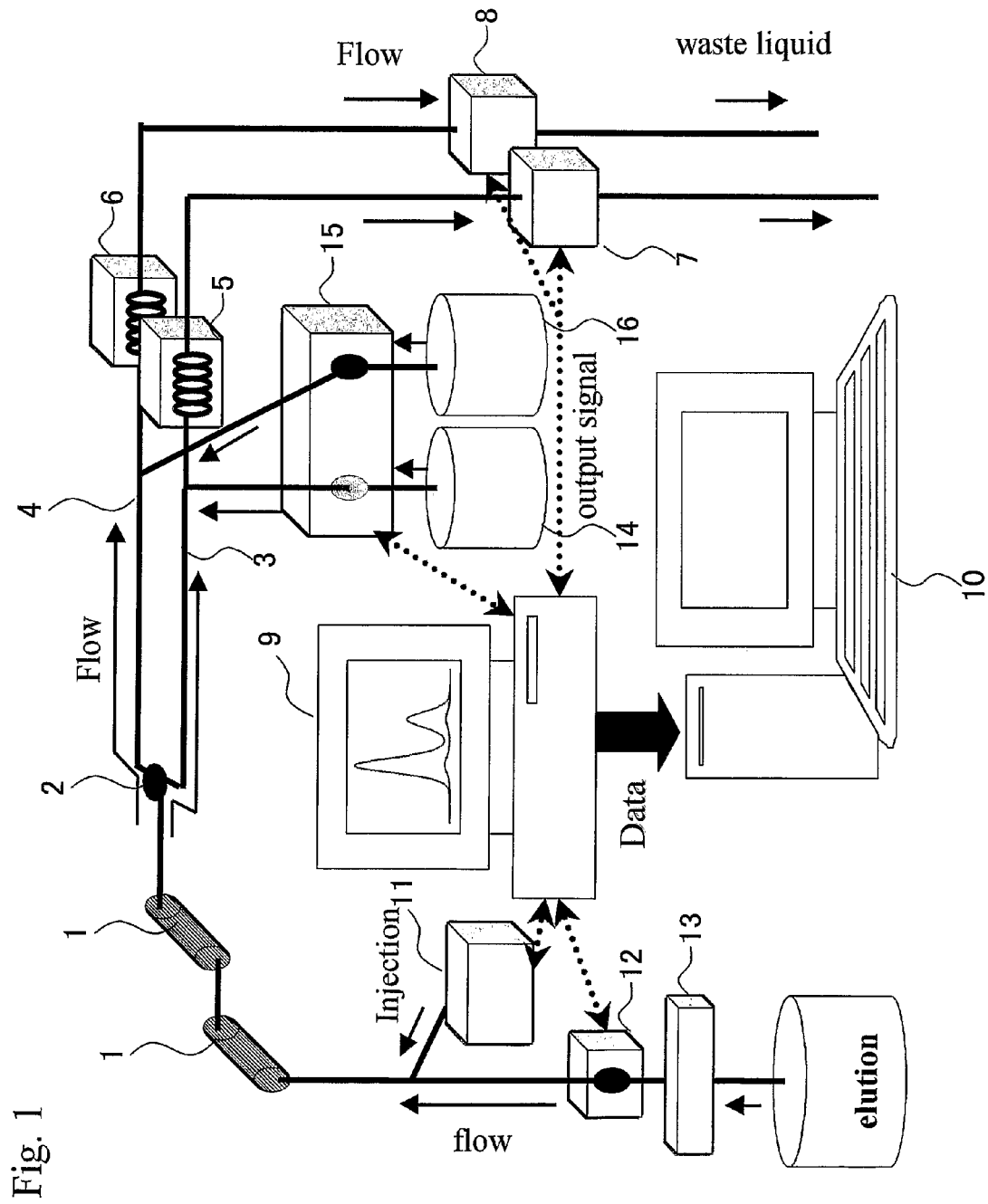
FIG. 1 is a diagram showing a system configuration of a lipoprotein analyzer which quantifies cholesterol and triglycerides contained in lipoprotein particles of a subject sample.

A lipoprotein analyzer to which an analytical method and an analytical program of the present invention are applied comprises, for example, a column 1 for isolating a lipoprotein component contained in a subject sample, a splitter 2 for splitting an eluent buffer containing lipoprotein particles eluted from the column 1 into 2 portions, a first channel 3 and a second channel 4 both of which are split by the splitter 2, a cholesterol (hereinafter, referred to as "TC") reaction part 5 placed on the first cannel 3, a triglycerides (hereinafter, referred to as "TG") reaction part 6 placed on the second channel 4, a TC detection part 7 positioned downstream of the TC reaction part 5 on the first channel 3, a TG detection part 8 positioned downstream of the TG reaction part 6 on the second channel 4, a system controller 9 which acts so as to control the operation of this system and to which signals from the TC detection part 7 and the TG detection part 8 are input, and an arithmetic unit 10 connected to the system controller 9, as shown in FIG. 1. The subject sample used herein is not specifically limited and refers to a sample derived from an organism such as serum, plasma, a spinal fluid, a tissue fluid, or a lymph fluid, as well as a sample containing secretory particles derived from cell culture.

The lipoprotein analyzer also comprises a sampler 11 for supplying a serum sample to the column 1, a first pump 12 for supplying the eluent buffer to the column 1, and a degasser 13 for removing a gas from eluent buffer to be supplied to the column 1 by the first pump 12.

Although the column 1 used for this lipoprotein analyzer is not specifically limited, it is particularly preferable to use a column to which a filler for gel filtration is packed. In particular, an example of the column 1 may be a column packed with a filler whose average fine pore size is 800 to 1200 angstroms. When a filler whose average fine pore size is less than 800 angstrom is used, it is difficult to permeate lipoprotein particles having a large particle size such as CM or VLDL into the fine pores. On the other hand, when a filler whose average fine pore size is more than 1200 angstrom is used, an ability thereof to isolate lipoprotein particles having a small particle size such as LDL or HDL is reduced. Thus it is preferable to use a filler whose average fine pore size is 800 to 1200 angstroms as described above. Among others, a filler whose average fine pore size is 900 to 1100 angstroms is excellent in its isolation capacity, so that eventually allows for analysis of lipoproteins with high precision.

In addition, the filler is required to be selected so as to have a sufficient mechanical strength to withstand the application thereof to the liquid chromatography. Examples of such fillers include, for example, silica gel, polyvinyl alcohol, polyhydroxymetacrylate, and other materials based on hydrophilic resins (for example, TSKgel Lipopropak, trade name, produced by Tosoh Corp.).

Examples of the eluent buffers include phosphate buffer solutions, tris-buffer solutions, bis-tris buffer solutions and the like, but are not specifically limited thereto as long as the solution can isolate lipoprotein particles. Concentrations of the buffer solution is preferably within a range of 20 to 200 mM, and more preferably 50 to 100 mM, since a concentration of the buffer solution less than 20 mM is not sufficient to provide a suitable buffering capacity and a concentration more than 200 mM may inhibit a reaction between the an enzyme reagent described below and TC or TG. A pH value of the buffer solution is 5 to 9, and more preferably 7 to 8, since the pH value less than 5 or more than 9 may inhibit the reaction with the enzyme reagent as described above. However, the pH value is not limited thereto as long as the measurement of the TC and/or TG is performed without the enzyme.

The TC reaction part 5 is connected via the second pump 15 to a TC reagent reservoir 14 containing a reagent which is used for quantifying TC included in an eluent buffer having lipoprotein particles eluted from the column 1. Examples of the reagents for quantifying TC include, but not specifically limited to, an enzyme-dye reagent obtained by combining an enzyme such as cholesterol esterase, cholesterol oxidase, or peroxidase with a dye such as N-ethyl-N-(3-methylphenyl)-N'-succinylethylenediamine, 4-aminoantipyrin, or N-ethyl-N-(3-sulfopropyl)-m-anisidine, for example. Examples of such reagents which can preferably be used are commercially available determiner L TCII (Kyowa Medex Co., Ltd.) and type L CHO.H (Wako Pure Chemical Industries Ltd.) principal upstream cause. These reagents react with TC to provide reaction products emitting, absorbing or fluorescence which is detectable by a spectroscope such as a fluorescence detector or a ultraviolet-visible light detector.

The TG reaction part 6 is connected via the second pump 15 to a TG reagent tank 16 containing a reagent which is used for quantifying TG included in an eluent buffer having lipoprotein particles eluted from the column 1. Examples of the reagents for quantifying TG include, but not specifically limited to, an enzyme-dye reagent obtained by combining an enzyme such as ascorbate oxidase, glycerol kinase, glycerol-triphosphate oxidase, lipoprotein lipase, and peroxydase with a dye such as quinone-based chromophoric dye, for example. Examples of the quinone-based chromophoric dyes include an oxidative condensate of N-ethyl-N-(3-methylphenyl)-N'-succinylethylenediamine or N-ethyl-N-(3-sulfopropyl)-m-anisidine and 4-antiaminopyridine. Examples of such reagents which can preferably be used are commercially available determiner L TGII (Kyowa Medex Co., Ltd.) and type L TG·H (Wako Pure Chemical Industries Ltd.).

Each of the TC reaction part 5 and the TG reaction part 6 is provided with a reaction coil for controlling a temperature during the reaction of the above described reagent with TC or TG. A reaction temperature of the above described reagent and TC or TG in the reaction part 5 or the reaction part 6 is 35 to 50° C., and preferably 45 to 50° C., since the reaction temperature less than 35° C. may be insufficient to carry out the reaction and the reaction temperature more than 50° C. may result in the deterioration of the enzyme during the reaction thereof.

The TC detection part 7 is provided with, for example, an ultraviolet-visible light detector for detecting an absorbance of the reaction product produced by the reaction between TC and the reagent in the TC reaction part 5. The TG detection part 8 is provided with, for example, an ultraviolet-visible light detector for detecting an absorbance of the reaction product produced by the reaction between TG and the reagent in the TG reaction part 6. For example, when a quinone-based chromophoric dye is used as the above described reagent, a measurement wave length of the ultraviolet-visible light detector may be 540 to 560 nm.

Figure 2:
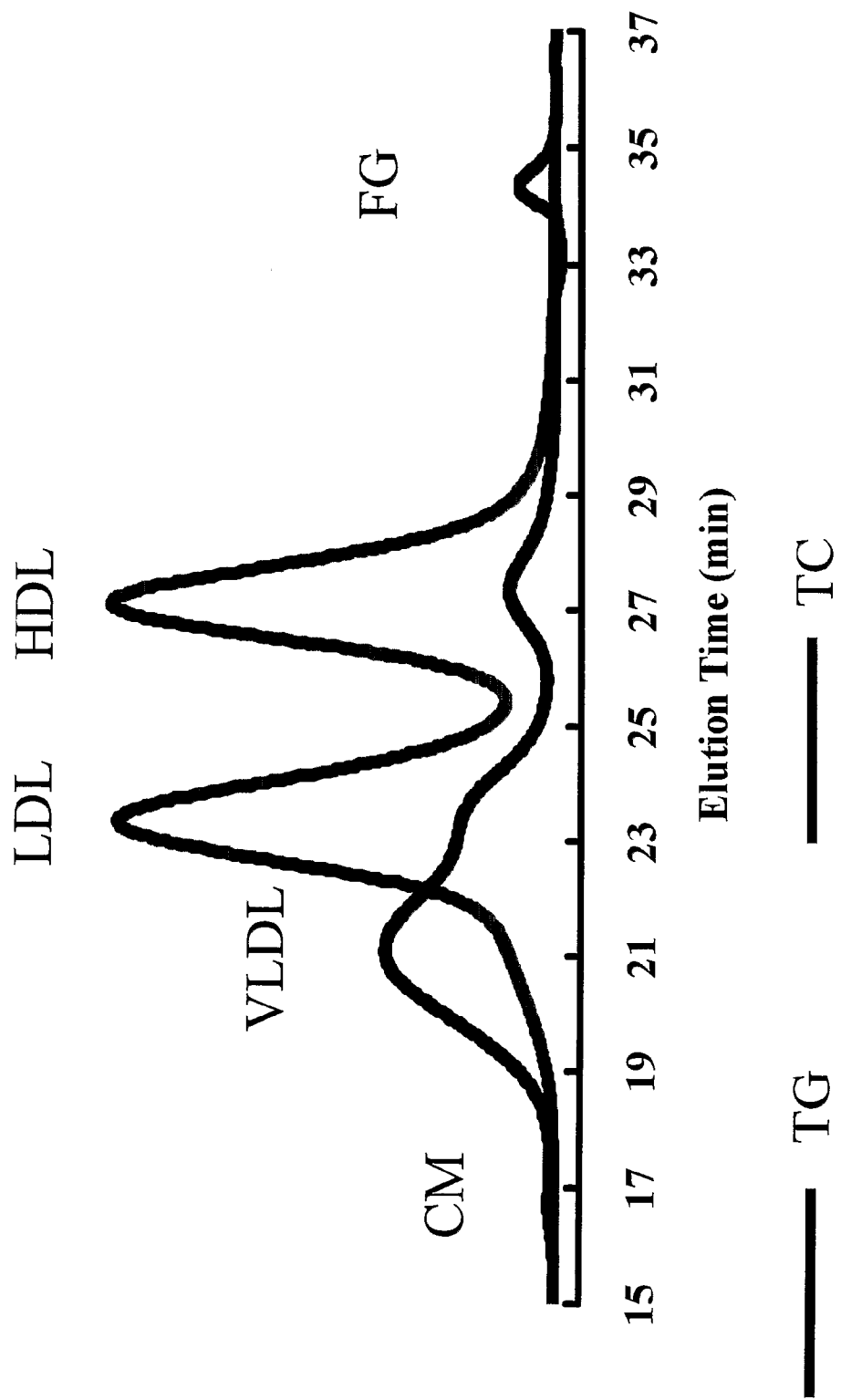
FIG. 2 is a characteristic diagram showing a cholesterol chromatogram together with a triglyceride chromatogram, with a horizontal axis representing an elution time (min.) and a vertical axis representing a detected value (mV)

The system controller 9, to which output signals from the TC detection part 7 and the TG detection part 8 are input, has the function of outputting a TC chromatogram and a TG chromatogram as a result. A chromatogram output from the system controller 9, with a horizontal axis representing an elution time (min.) and a vertical axis representing a detected value (mV), can display a TC chromatogram with a TG chromatogram superimposed thereon as shown in FIG. 2, for example.

As the arithmetic unit 10, it is possible to use a computer on which an analytical program as described below is installed, for example. The arithmetic unit 10 is connected to the system controller 9, and has functions of carrying out data processing on the chromatogram being output from the system controller 9 by the use of the analytical program, separating lipoprotein particles contained within the subject sample into 20 component peaks, and calculating amounts of TC and TG. The arithmetic unit 10 may also be connected to the system controller 9 via an information communication circuit network such as the Internet, LAN, or an intranet.

According to the above described lipoprotein analyzer, various lipoproteins are firstly classified depending on the particle size thereof through the column 1, and then TC and TG which are contained in the eluent buffers eluted from the column 1 are quantified. Therefore, the lipoprotein analyzer is able to quantify TC and TG for every subclass of lipoproteins depending on a resolution of the column 1.

The lipoproteins are classified into a plurality of classes based on differences in the properties such as particle size, hydration density, degrees of electrophoresis and the like. The present analyzer separates lipoprotein particles included in the serum sample into 20 component peaks in accordance with the analytical program as described below.

Now the analytical program will be described. The analytical program controls the arithmetic unit 10 following a flowchart comprising Step 1 and Step 2.

Step 1 is to firstly input a chromatogram as an input signal which is output from the system controller 9 via input means of the arithmetic unit 10. That is, the analytical program executes the computer as detection means for input a chromatogram as an input signal which is output from the system controller 9 at Step 1.

Step 1 will now be described in detail. Firstly, a TC chromatogram and a TG chromatogram as shown in FIG. 2 are input via input means of the arithmetic unit 10, and then the chromatograms and/or numeric data supporting the chromatograms are stored in an intrinsic memory of the arithmetic unit 10 or recorded on a recording medium which is recordable by the arithmetic unit 10.

Next, Step 2 is to perform data processing of the input chromatograms and then to classify the obtained results into 20 component peaks in order to calculate the Gaussian approximated curves. That is, the analytical program executes the computer as data processing means for calculating the Gaussian approximated curves at Step 2. The data processing means allows for separation of the chromatogram which is input at Step 1 into independent 20 peaks. In the following description, the independent 20 peaks are referred to as G1 to G20 in decreasing order of size. G1 and G2 are component peaks corresponding to chylomicrons (CM), G3 to G7 are component peaks corresponding to very low density (specific gravity) lipoproteins (VLDL), G8 to G13 are component peaks corresponding to low density lipoproteins (LDL), and G14 to G20 are component peaks corresponding to high density lipoproteins (HDL). Among component peaks corresponding to VLDL, G3 to G5 indicate large VLDL, G6 indicates medium VLDL, and G7 indicates small VLDL.

Among component peaks corresponding to LDL, G8 indicates large LDL, G9 indicates medium LDL, G10 indicates small LDL, and G11 to G13 indicate very small LDL. Among component peaks corresponding to HDL, G14 and G15 indicate very large HDL, G16 indicates large HDL, G17 indicates medium HDL, G18 indicates small HDL, and G19 and G20 indicate very small HDL.

The data processing means at Step 2 is to separate or classify the chromatogram or numeric data which are input at Step 1 into 20 component peaks and then to allow the arithmetic unit 10 to perform calculations of the Gaussian approximated curves including G1 to G20. The 20 component peaks are those being separated in accordance with the size of lipoprotein particles.

Figure 3:
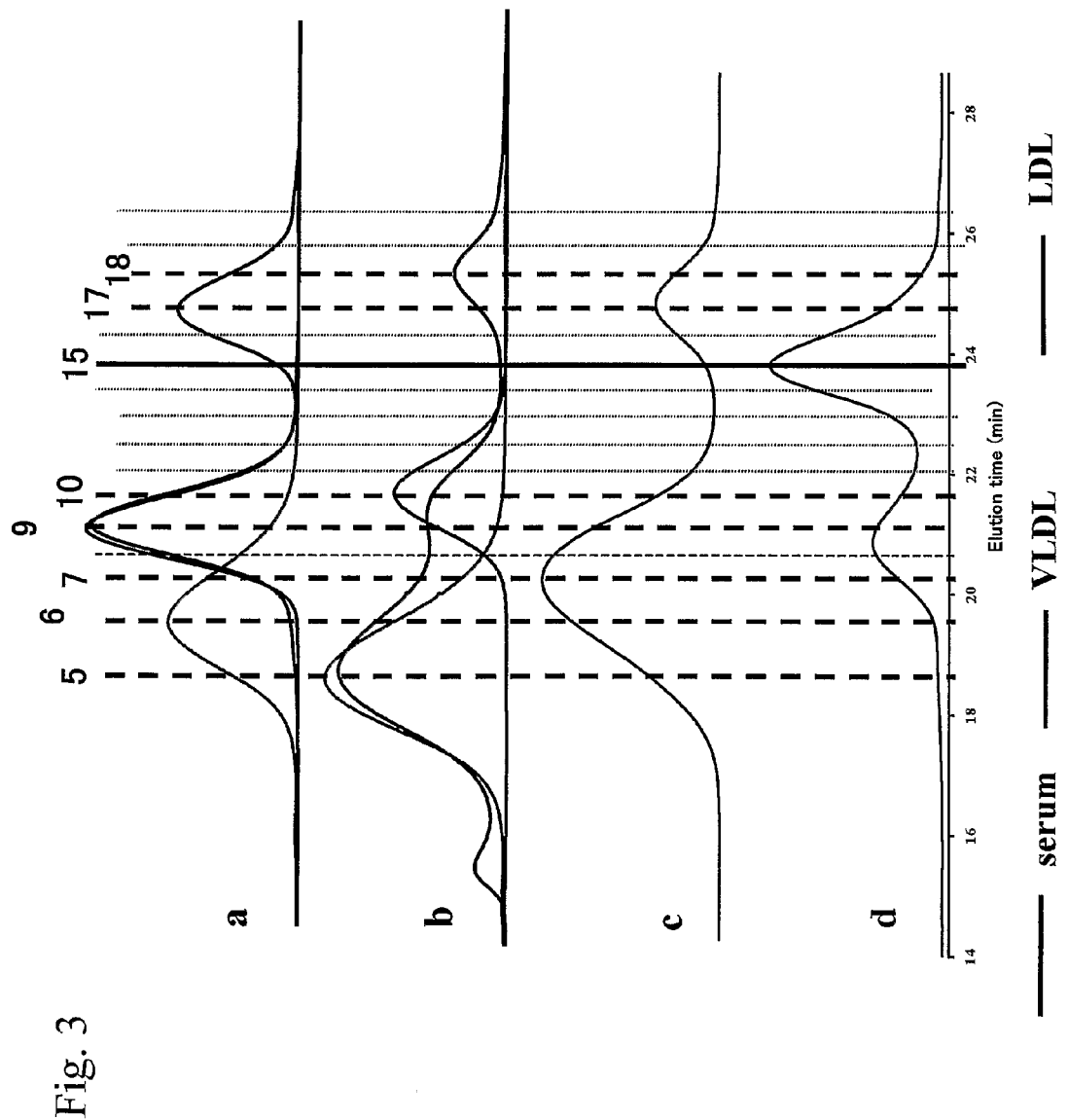
FIG. 3 is a characteristic diagram showing data supporting the definition of an anchor peak, obtained by the use of two TSKgel LipopropalXL columns (produced by Tosoh Corp.)

Respective peak positions of respective 20 component peaks are defines as described below. As for the respective 20 peaks comprising G1 to G20, peak positions (elution times) of standard peaks (anchor peaks) are firstly determined, and then peak positions of peaks other than the anchor peaks (extra essential peaks) are determined. Specifically, G5, G6, G7, G9, G10, G15, G17, and G18 are defined as anchor peaks and G1 to G4, G8, G11 to G14, G16, G19, and G20 are defined as extra essential peaks by way of examples. FIG. 3 shows an example of data which support the definition of G5, G, G7, G9, G10, G15, G17, and G18 as anchor peaks.

Since particles of VLDL size, LDL size, and HDL size in the mormolipidemic middle-aged men (age 30s to 40s) population are respectively distributed in certain ranges, each of elution positions thereof is determined to be at G6, G9, and G17 among these anchor peaks (see FIG. 3(a)). Specifically, TC chromatograms and TG chromatograms as shown in FIG. 2 are obtained from serum samples which have been collected from a plurality of mormolipidemic middle-aged men (age 30s to 40s). On the obtained chromatograms, peaks corresponding to major categories VLDL, LDL, and HDL are appeared in this order. An average value of the peak position corresponding to each of VLDL, LDL, and HDL on the chromatograms obtained from the plurality of mormolipidemic middle-aged men is calculated, and the average VLDL size, average LDL size, and average HDL size are defined as elution positions at G6, G9, and G17 respectively.

In the case where a lipoprotein lipase activity is absent or very low, triglycerides of the TG-rich lipoprotein is not decomposed, and VLDL still having a large size remains in blood. Therefore, particles of the VLDL size in the case where the lipoprotein activity is absent or very low are significantly larger than those of the mormolipidemic men, and are distributed within a certain size range. An average elution position of the VLDL is defined as an elution position of G5 among the anchor peaks (see FIG. 3(b)).

In addition, following the function of cholesterol ester transfer protein presenting in blood, triglycerides are transferred from VLDL to LDL while cholesterol esters are transferred from LDL to VLDL. LDL becomes triglyceride-rich particles, and triglycerides in LDL are decomposed by hepatic lipase and LDL becomes smaller. Particle sizes of LDL in the case where a lipoprotein lipase activity is absent or very low are significantly smaller than a LDL size of the mormolipidemic men, and are distributed within a certain size range. Thus, an average elution position of this LDL is defined as an elution position of G10 among the anchor peaks (FIG. 3(b)).

In addition, in the case where the lipoprotein lipase activity is absent or very low, triglycerides are transferred from LDL or VLDL to HDL while cholesterol esters are transferred from LDL to LDL or VLDL. Consequently, HDL becomes rich in triglycerides, and triglycerides in HDL are decomposed by hepatic lipase and thus the HDL becomes smaller. Therefore, particles of HDL size in the case where the lipoprotein lipase activity is absent or very low are significantly smaller than those of the mormolipidemic men, and are distributed within a certain range. Thus, an average elution position of this HDL is defined as an elution position of G18 among anchor positions (see FIG. 3(b)).

Still further, in the case suffering from cholesterol ester transfer protein deficiency, cholesterol esters are not transferred from HDL to LDL or VLDL while triglycerides are not accepted from LDL or VLDL, so that HDL becomes rich in cholesterol and also becomes larger in size. Especially in the cholesterol ester transfer protein deficiency, HDL includes little triglycerides. Particles of HDL size in the case where the cholesterol ester transfer protein is completely deficient are significantly larger than those of the mormolipidemic men, and are distributed within a certain size range. Thus an average elution position of this HDL is defined as an elution position of G15 among anchor peaks (see FIG. 3(d)).

Still further, in the type III hyperlipidemia with ApoE2/2, substitution of Cys for Arg at the 158th position results in conformational variation of a site binding to LDL receptors (ApoB/E), LDL receptor associated proteins, and VLDL receptors which have ApoE as ligands, so that incorporation of small VLDL (remnant) is reduced, components corresponding to the small VLDL are increased in blood, and consequently specific peaks are observed. Thus, an average elution position of the VLDL in this case is defined as an elution position of G7 among anchor peaks (see FIG. 3(c)). The elution position of the small VLDL is corresponding to that of intermediate density lipoproteins (IDL) isolated by ultracentrifugation as a fraction with density between 1.006 g/ml and 1.019 g/ml from a plurality of human subjects including type III hyperlipidemia with apo E2/2 (see Shinichi Usui, Yukichi Hara, Seijin Hosaki, and Mitsuyo Okazaki, Journal of Lipid Research, Volume 43, p 805-814, (2002)). Further, the cholesterol content in the IDL fraction highly correlates to the cholesterol content in the small VLDL in the present invention. Therefore, the small VLDL determined by anchor peak G7, which is remarkably increased in the type III hyperlpidemia with apo E2/2 corresponds to remnant lipoproteins and/or IDL.

Although the data shown in FIG. 3 are obtained by using two TSKgel LipopropakXL columns (produced by Tosoh Corp.), data obtained by using other columns may also be used as data which support the definition as the anchor peaks.

Figure 4:
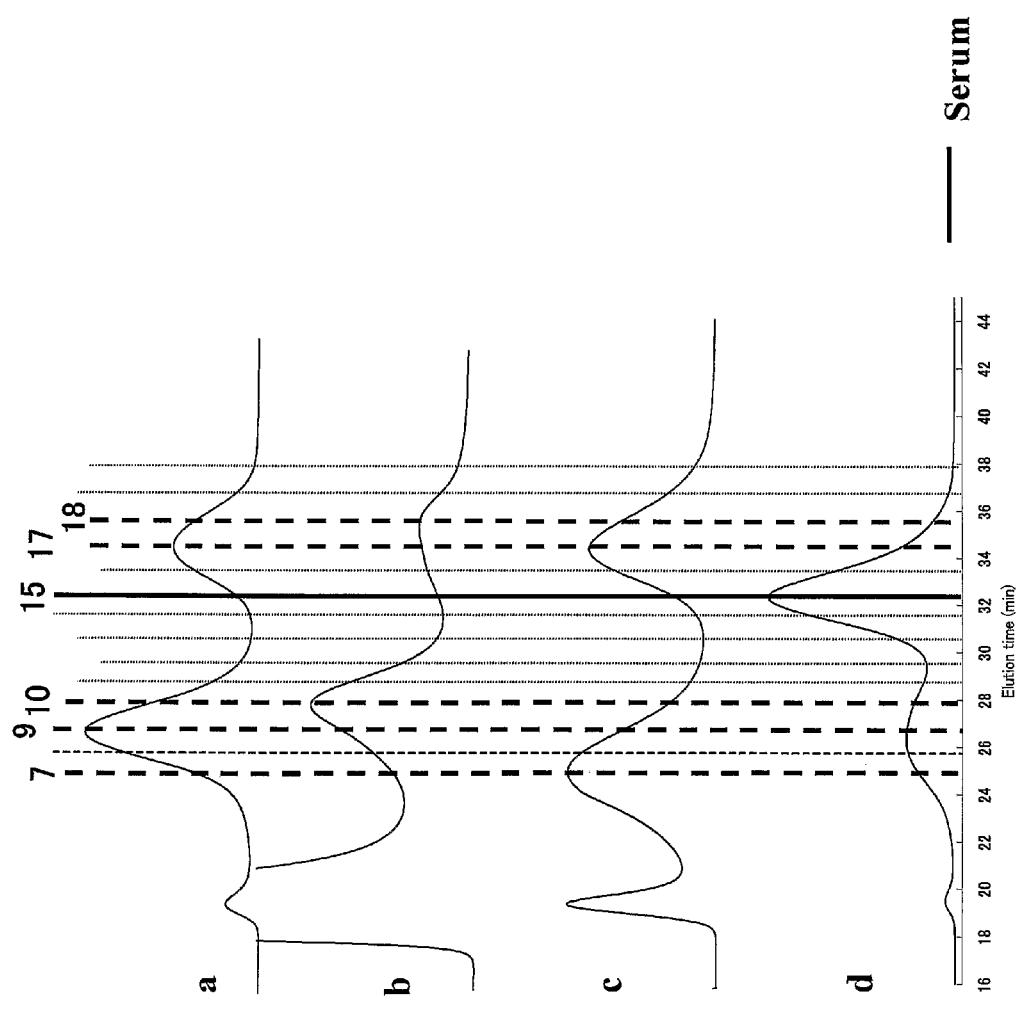
FIG. 4 is a characteristic diagram showing data supporting the definition of an anchor peak, obtained by the use of a Superose 61R 10/30 column (produced by Pharmacia)

For example, data can be similarly obtained by using a Superose 61R 10/30 column (produced by Pharmacia) as shown in FIG. 4, and thus anchor peaks can be defined based on these data. In this case, elution positions of G9 and G17 can be defined from a profile of mormolipidemic middle-aged men (age 30s to 40s) (FIG. 4(a)). Elution positions of G10 and G18 can be defined from a profile of a case where the lipoprotein lipase activity is absent or very low (FIG. 4(b)). An elution position of G7 can be defined from a profile of a case of the type III hyperlipidemia with ApoE2/2 (FIG. 4(c)). An elution position of G15 can be defined from a profile of a case where the cholesterol ester transfer protein is completely deficient (FIG. 4(d)).

Figure 5:
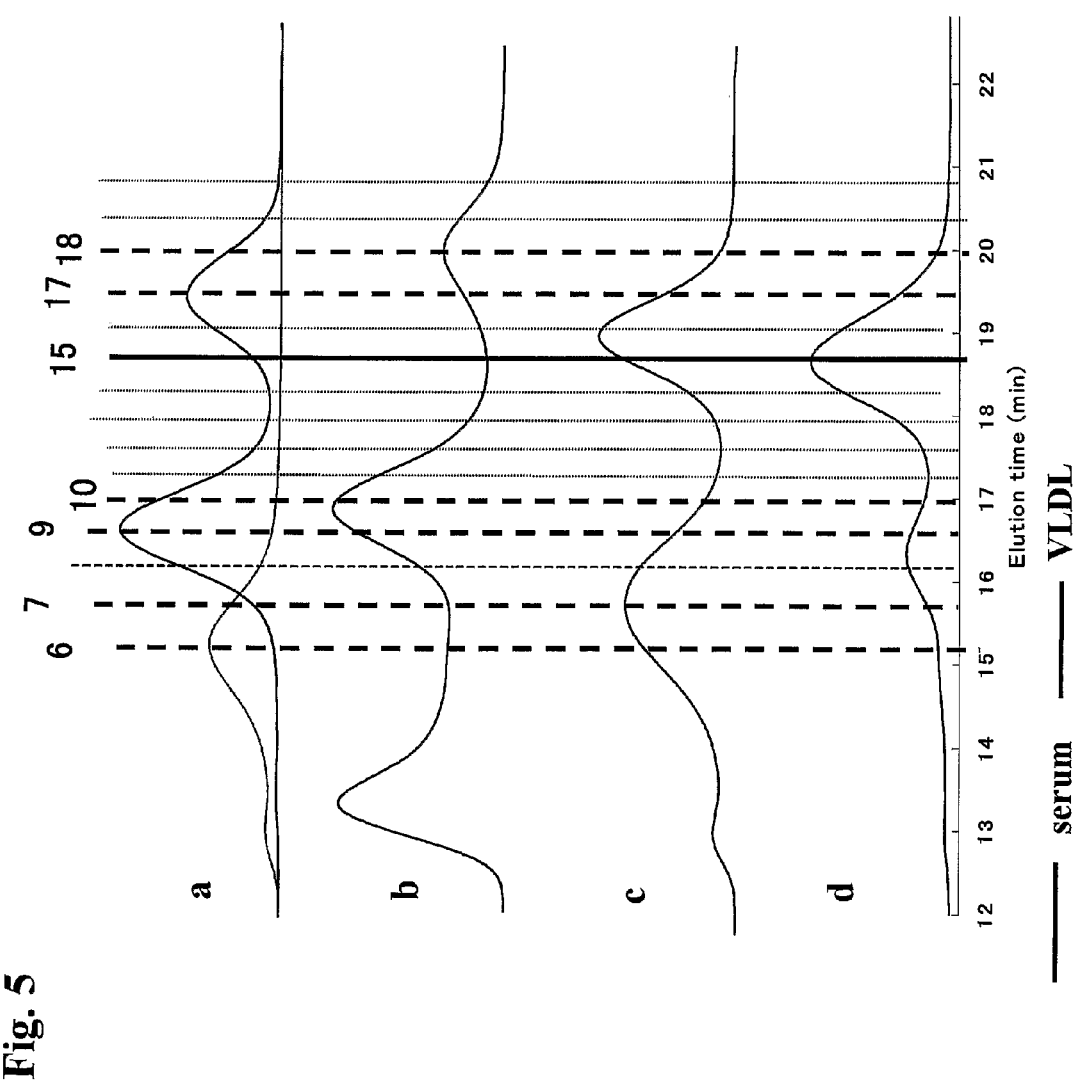
FIG. 5 is a characteristic diagram showing data supporting the definition of an anchor peak, obtained by the use of a SkylightPak-LDL column (produced by Skylight Biotech Inc)

For further example, data can be similarly obtained by using a SkylightPak-LDL column (produced by Skylight Biotech Inc.) as shown in FIG. 5, and thus anchor peaks can be defined based on these data. In this case, elution positions of G6, G9 and G17 can be defined from a profile of mormolipidemic middle-aged men (age 30s to 40s) (FIG. 5(a)). Elution positions of G10 and G18 can be defined from a profile of a case where the lipoprotein lipase activity is absent or very low (FIG. 5(b)). An elution position of G7 can be defined from a profile of a case of the type III hyperlipidemia with ApoE2/2 (FIG. 5(c)). An elution position of G15 can be defined from a profile of a case where the cholesterol ester transfer protein is completely deficient (FIG. 5(d)).

As described above, respective elution positions are defined provided that G5, G6, G7, G9, G10, G15, G17, and G18 are anchor peaks.

Next, as for extra essential peaks, positions and widths of the peaks are mathematically determined. The extra essential peaks are necessary for analyzing component peaks by Gaussian approximation in which the size and distribution of the component peaks are fixed (time and width are fixed). In terms of LDL and HDL, a distribution width of component peaks comprising anchor peaks and extra essential peaks is assumed to be almost the same to each other, and extra essential peaks are also assumed to be located between the anchor peaks at almost equal intervals. Four extra essential peaks (peaks 11 to 14) are set between G10 and G15, one extra essential peak (peak 8) is set between G7 and G9, one extra essential peak (peak 16) is set between G15 and G17, and two extra essential peaks (peaks 19 and 20) are set after G18. Positions of extra essential peaks (peaks 16 to 20) belonging to HDL can be defined with reference to correspondence between the peak observation frequencies in the normal population and the experimental values obtained by performing re-chromatography, in the analysis which uses another HDL-specific column (see Okazaki M et al., J. Biochem., 1982; 92:517-524).

Positions of component peaks G8 to G20 were determined to be at almost equal intervals and widths thereof were also determined to be almost equal. Component peaks 2, 3, 4 were necessary to perform Gaussian approximation between a peak 1 at Void and G5 of an anchor peak, and were determined in accordance with a rule between the peak intervals and the widths.

In addition, a minimum value of the component peak widths can be defined as a free glycerol (particle whose molecular weight is 92 and whose size is homogeneous, FG as presented in FIG. 2) width obtained from the analytical system, and a maximum value thereof can be defined as two times as large as an interval between adjacent component peaks.

As for 20 component peaks, the peak width can be set to a numeric value obtained by the following equation, SD (min.)=half width of peak (sec.)/143. Specifically, values as described below are input or preset as the peak widths of 20 component peaks: 033 min. for G01; 0.40 min. for G02; 0.55 min. for G03; 0.55 min. for G04; 0.55 min. for G05; 0.50 min. for G06; 0.40 min. for G07; 0.38 min. for G08; 0.38 min. for G09; 0.38 min. for G10; 0.38 min. for G11; 0.38 min. for G12; 0.38 min. for G13; 0.38 min. for G14; 0.38 min. for G15; 0.38 min. for G16; 0.38 min. for G17; 0.38 min. for G18; 0.38 min. for G19; and 0.48 min. for G20.

The data processing means at Step 2 can be carried out by applying a Gaussian curve fitting computation algorithm, for example. According to the Gaussian curve fitting computation algorithm, 20 component peaks can be obtained as described below.

That is, firstly, given that a single peak on a chromatogram takes a form of a symmetric gaussian distribution, a peak height h(t) at a time t can be expressed as $$h(t) = H \times \exp(-(t-T)^2/2\sigma^2)$$

where T is a position of a peak and $\sigma$ is a width (standard deviation) (H is a maximum value of the peak heights). It is known that the peak also takes a form of (1) Peason VII, (2) Lorentzian, (3) exponentially modified Gaussian, (4) Weibull, (5) bi-Gaussian, (6) poisson, (7) Gram-Charlier, (8) combination of Gauss and Cauchy functions, (9) combination of statistical moments, or (10) cam-driven analog peak, so that it is possible to assume that the peak takes a form of any of these (1) to (8).

A height of the n th peak, $h_n(t)$, can be expressed as $$h_n(t) = H_n \times \exp(-(t-T_n)^2/2\sigma_n^2) \quad \text{I}$$

where $T_n$ is a position of the n th peak and $\sigma_n$ is a width (standard deviation) ($H_n$ is a maximum value of the n th peak (height)).

Given that $\exp(-(t-T_n)^2/2\sigma_n^2) = G_n(t)$, a formula I can be expressed as $$h_n(t) = H_n \times G_n(t) \quad \text{II}$$

Given that N peaks are respectively independent, a synthetic curve at a time t A(t) is expressed as $$A(t) = h1(t) + h2(t) + \ldots + hn-1(t) + hn(t) \quad \text{III}$$
$$= H1 \times G1(t) + H2 \times G2(t) + \ldots + Hn-1 \times Gn-1(t) +$$
$$Hn \times Gn(t).$$

Given that the number of data points is m, the above described formula III can be expressed as follows in m different ways:

$$A(t1) = H1 \times G1(t1) + H2 \times G2(t1) + \ldots + Hn-1 \times Gn-1(t1) + Hn \times Gn(t1);$$

$$A(t2) = H1 \times G1(t2) + H2 \times G2(t2) + \ldots + Hn-1 \times Gn-1(t2) + Hn \times Gn(t2);$$

…; and $$A(tm) = H1 \times G1(tm) + H2 \times G2(tm) + \ldots + Hn-1 \times Gn \times 1(tm) + Hn \times Gn(tm).$$

Given that an actual curve of an chromatogram at a time t is indicated by R(t), a curve fitting method is used for determining the peak numbers n, peak positions T, and widths (standard deviations) a so as to obtain R(t)=A(t). Practically, since a formula R(t)=A(t) can not be achieved at any time by a linear method of least squares, parameters by which the sum of $(R(t)-A(t))^2$ becomes minimum are determined.

In addition to the curve fitting method, it is also possible to apply an iterative method (such as Fletcher Powell, Marquardt, Newton-Raphson, Simplex minimization, Box-Complex method) for example. However, these procedures other than the curve fitting method have disadvantages as follows, that is: an initial value has an effect on the calculation result; it is necessary to assume previously whether the curve corresponds to Gaussian or to Lorentzian; and convergence is difficult to achieve when the number of peaks are larger (4 or more). Therefore, it is very important to know how to determine an initial value which is closer to a true value. Procedures such as (1) factor analysis, (2) moments analysis, (3) orthogonal polynominal analysis, and (4) inverse diffusion model have recently been reported as a peak separation method for overcoming these disadvantages; and can also be applied to the present algorithm.

Since $t_i$ (i=1, 2, …, m) is a constant, any $G_n(t_i)$ also becomes a constant. Thus, the above described formula III can be expressed as follows in m different ways;

$$A(t1) = H1 \times G1(t1) + H2 \times G2(t1) + \ldots + H19 \times Gn-1(t1) + H20 \times G20(t1);$$

$$A(t2) = H1 \times G1(t2) + H2 \times G2(t2) + \ldots + H19 \times Gn-1(t2) + H20 \times G20(t2);$$

…; and $$A(tm) = H1 \times G1(tm) + H2 \times G2(tm) + \ldots + H19 \times G19(tm) + H20 \times G20(tm).$$

Given that R(t)=A(t), m primary expressions each of which comprises 20 unknown numbers H1, H2, …, H19, and H20 can be obtained. If m=20, then a solution can be found by solving the primary expression.

Although the number of data points is not 20 in the actual data, 20 points at which calculation is easily carried out at high speed (for example, 20 peak positions each of which exist in respective 20 component peaks) are conveniently selected for calculation in the present algorithm. In the present algorithm, the number of data points may not be selected to be 20 points but may determined by a method of least squares.

According to the flowchart comprising Step 1 and Step 2 as described above, a chromatogram which is output from the system controller 9 (for example, a chromatogram shown in FIG. 2) can be separated into 20 component peaks. A profile obtained by the separation into 20 component peaks, which shows a noticeable correlation with visceral fat area (VFA), is effectively utilized for examining the risk of diseases caused by accumulation of visceral fat.

Examples of diseases caused by the accumulation of visceral fat include arteriosclerotic diseases represented by an ischemic heart disease, for example. That is, as a result of over-nutrition or low physical activity associated with recent changes in life-style which leads to fat accumulation and obesity, the incidence of arteriosclerotic diseases represented by an ischemic heart disease have been increased due to the accumulation of numerous risk factors. This kind of disease is developed by inducing an insulin resistance due to a hereditary predisposition causing the insulin resistance combined with an acquired factor such as obesity. It is important to consider intra-abdominal visceral fat accumulation as a principal upstream cause. The intra-abdominal accumulation of visceral fat caused by obese people as well as by not-obese people closely contributes to the onset of diabetes, hypertension, and coronary artery disease (CAD). Thus, examples of diseases caused by the accumulation of visceral fat include diabetes, hypertension, hyperlipidemia, and coronary artery disease.

In a method for diagnosing diseases caused by accumulation of visceral fat according to the present invention, for example, the visceral fat area is proportionally related to a cholesterol content in a large, medium, or small subclass of VLDL and to a medium, small, or minimum subclass of LDL, while the visceral fat area is inversely related to a cholesterol content in a large or medium subclass of HDL. In other words, a disease due to the accumulation of visceral fat is diagnosed by an increase in a cholesterol content within a large, medium, or small subclass of VLDL and within a medium, small, or very small subclass of LDL, and by an decrease in a cholesterol content within a large or medium subclass of HDL.

A high level of LDL cholesterol is one of the important risk factors. When a concentration of the LDL cholesterol is normal (LDL-C<130 mg/dL), a concentration of cholesterol in the small and very small LDL subclasses are proportionally related to the visceral fat area, while a concentration of cholesterol in the large LDL subclass is inversely related to the visceral fat area. This means that an antiatherogenetic LDL subclass is included in the LDL and that the large LDL subclass acts so as to inhibit the onset of arterial sclerosis. Although a component peak of the large LDL subclass is determined to be an extra essential peak and also determined as a transition component between VLDL and LDL, the component peak can be newly estimated as a new subclass having a clinical meaning according to the present invention. In other words, the onset of arterial sclerosis due to the visceral fat accumulation can be diagnosed by cholesterol content at a component peak of the large LDL subclass.

In addition, it is observed in the coronary artery disease that a cholesterol concentration of the small VLDL subclass increases, cholesterol concentrations of the small and very small LDL subclass also increase, and a cholesterol concentration of the large HDL subclass decreases, so that it is possible to diagnose the coronary artery disease by measuring cholesterol concentrations in the small VLDL, small and very small LDL, and large HDL subclasses.

Therefore, a method for diagnosing the coronary artery disease can be provided according to the present invention. The method for diagnosing the coronary artery disease utilizes the separated 20 component peaks according to the flowchart comprising Step 1 and Step 2 as described above. Specifically, the method for diagnosing the coronary artery disease comprises steps of: analyzing lipoprotein contained in a subject sample taken from a subject to be diagnosed according to the flowchart comprising Step 1 and Step 2 described above to obtain 20 component peaks derived from the subject; and calculating a value according to any one formula selected from (I) to (V):

$$Vs+Ls-Hs; \quad (I)$$

$$Vs+Ls; \quad (II)$$

$$Ls; \quad (III)$$

$$(Vs+Ls)/Hs; \text{ and} \quad (IV)$$

$$Ls/Hs, \quad (V)$$

wherein: "Vs" represents the cholesterol content in small VLDL; "Ls" represents the sum of cholesterol contents in small LDL and very small LDL; and "Hs" represents the cholesterol content in large HDL.

The value obtained by the method for diagnosing the coronary artery disease is useful for a clinical examination concerning the coronary artery disease. In the method for diagnosing the coronary artery disease, the step of analyzing may comprise a step of comparing the calculated value with a reference value. The reference value may be set to predetermined numerical value, which is calculated based on results of analysis for a group of normal subject and a group of the coronary artery disease case. The reference value may be set with respect to each age groups, ethnic groups, gender and so on.

A component peak of the small VLDL subclass being significantly increased in the coronary artery disease is an anchor peak which is determined from a VLDL size derived from the type III hyperlipidemia with Apo E2/2, and thus corresponds to a remnant being increased in the type III hyperlipidemia with Apo E2/2, so that it is recognized that the remnant which is also an important risk factor for the coronary artery can be estimated from a component peak corresponding to small VLDL subclass in the present program.

EXAMPLES

The present invention is further explained in detail using examples. However, the technical scope of the present invention is not limited by the following examples.

Example 1

Methods

Subjects

Sixty-two men (aged 22 to 67 years) were enrolled in this study, which included 15 healthy volunteers and 47 hospitalized patients in Osaka University Hospital. All of the subjects gave their informed consent before entering the study according to the Osaka University Hospital ethics committees. All patients had no severe hepatic or renal diseases, and none of them had any medication known to affect insulin action or serum lipoprotein levels. Venous blood was drawn after an overnight fasting. Serum samples were kept in a refrigerator and analyzed within 7 days after blood collection.

HPLC Method

In brief, 5 mL whole serum sample was injected into 2 connected columns (300k×7.8 mm) of TSKgel Lipopropa-kXL (Tosoh) and eluted by TSKeluent Lp-1 (Tosoh). The effluent from the columns was continuously monitored at 550 nm after an online enzymatic reaction with a commercial kit, Determiner L TC (Kyowa Medex). The cholesterol concentration in major lipoproteins and their subclasses was calculated by our own computer program, which was designed to process the complex chromatograms with the modified Gaussian curve fitting for resolving the overlapping peaks by mathematical treatment.

We determined the number, position, and width of each Gaussian component peak for subclass analysis to carry out a sufficient curve fitting analysis of various samples from animals and humans under the constant condition in which the peak width and position of each Gaussian curve were not changed. For this purpose, we first took priority to refer the mean particle size of VLDL and LDL of healthy normolipidemic men (n=28). Therefore, the positions of component peaks 6 and 9 corresponded to those of VLDL (36.8±2.5 nm) and LDL (25.5±0.4 nm) of healthy subjects, respectively. Similarly, the positions of peaks 5 and 10 were those of VLDL (44.5±2.1 nm) and LDL (23.0±0.5 nm) of extremely hypertriglyceridemic subjects>1000 mg/dL (n=7) with or without lipoprotein lipase (LPL), respectively. Peak 7 corresponded to LDL (or VLDL; 31.3±1.0 nm) of type III hyperlipidemia with apoE2/2 (n=5). Peak 15 was HDL (13.5±0.4 nm) of cholesterol ester transfer protein deficiency (n=6). Other component peaks (peaks 16 to 20) of HDL subclasses were based on the 5 subclasses determined by HPLC using a gel permeation column (G3000SW) with a separation range for only HDL. In addition to the 11 component peaks determined by some experimental background as described above, 9 additional peaks (peaks 1 to 4, 8, and 11 to 14) were introduced to obtain the best curve fitting analysis by changing only peak height of each Gaussian curve. The position of peak 8 (28.6 nm) was determined as the middle point between peak 7 and peak 9, representing a transition component from TG-rich remnant lipoproteins to LDL. Four peaks (peaks 11 to 14) were regularly inserted between peak 10 and peak 15 to make similar intervals from peak 8 to peak 20. Moreover, 3 peaks (peaks 2 to 4) at least needed to be introduced between a void volume (peak 1) and peak 5 to perform the best curve fitting. Alternative setting of additional peaks resulted in the decrease of the degree of curve fitting analysis on the original chromatogram. The conversion of elution time to particle diameter was performed using a column calibration curve, a plot of logarithm of the particle diameter of standard samples, latex beads (Magsphere Inc) 25 and 37 nm in diameter, and a high molecular weight calibrator (Pharmacia Biotech) containing thyroglobulin (17 nm), ferritin (12.2 nm), catalase (9.2 nm), albumin (7.1 nm), and ovalbumin (6.1 nm) against their elution times.

Other Clinical and Lipid Parameter Analysis

Serum TC and TG were determined enzymatically using commercial kits (Kyowa Medex). IDL-C was quantified by the heparin-$Ca^{2+}$ precipitation method. LDL-C was calculated from the formula of Friedewald et al. Uric acid (UA), fasting immunoreactive insulin (IRI), and plasminogen activator inhibitor (PAI)–1 were measured by enzymatic methods and by a double antibody radioimmunoassay, respectively.

Body fat distribution was determined by computed tomographic (CT) scanning (General Electric CT/T scanner, General Electric Co) in the supine position as described previously. The fat layer to the extraperitoneal region between skin and muscle was defined as subcutaneous fat area (SFA), with an attention range from −40 to −140 Hounsfield units. The intraperitoneal region, with the same density as SFA, was defined as the VFA. The SFA and VFA were measured at the level of the umbilicus.

Statistical Analysis

Data are expressed as mean±SD, unless stated otherwise. Correlations between various variables were presented as the Pearson correlation coefficient (r-value) with a P-value <0.05 considered to be statistically different.

<Results>

Clinical Characteristics and Lipid Levels of Studied Subjects

Clinical characteristics and lipid levels in 62 men in this study are shown in Table 1.

TABLE 1

Clinical characteristics, lipid and lipoprotein profiles of 62 men.

| | mean ± SD | min/max |
|---|---|---|
| AGE (years) | 43.8 ± 11.3 | 22/67 |
| Hight (cm) | 169.8 ± 6.3 | 152/181 |
| Weight (kg) | 77.5 ± 15.1 | 56/135 |
| BMI (kg/m$^2$) | 26.8 ± 4.6 | 21.0/43.1 |
| VFA (cm$^2$) | 129.2 ± 50.4 | 24.0/255.0 |
| SFA (cm$^2$) | 195.52 ± 97.89 | 55.0/512.0 |
| UA (mg/dl) | 6.4 ± 1.7 | 3.8/12.5 |
| IRI (μU/ml) | 9.3 ± 7.7 | 2.0/42.8 |
| PAI-1 (ng/ml) | 25.4 ± 18.6 | 5.0/75.7 |
| TC (mg/dl) | 212.6 ± 35.2 | 135.0/308.7 |
| TG (mg/dl) | 146.3 ± 88.3 | 41.5/416.0 |
| HDL-C (mg/dl) * | 45.0 ± 12.4 | 22.6/70.7 |
| LDL-C (mg/dl) † | 138.3 ± 34.5 | 61.1/211.5 |

* Determined by the precipitation method.
† Calculated value by the Friedewald equation.

A considerably wide range of anthropometric values was obtained, because they were recruited to cover a large spectrum of body fat values: body mass index (BMI) from 21 to 43 kg/cm$^2$, VFA from 24 to 255 cm$^2$, and SFA from 55 to 512 cm$^2$. Metabolic parameters showed a variation as compared reference values: UA from 3.8 to 12.5 mg/dL, IRI from 2 to 43 μU/mL, and PAI-1 from 5.0 to 75.7 ng/mL.

Analytical Performance of HPLC for Determination of Serum Cholesterol Levels in Major Lipoproteins and Their Subclasses We defined 3 VLDL subclasses (large, medium, and small), 4 LDL subclasses (large, medium, small, and very small), and 5 BDL subclasses (very large, large, medium, small, and very small) on the basis of lipoprotein particle size (diameter), as shown in Table 2: chylomicrons (>80 nm, peaks 1 to 2), VLDL (30 to 80 nm, peaks 3 to 7), LDL (16 to 30 nm, peaks 8 to 13), and HDL (8 to 16 nm, peaks 14 to 20).

TABLE 2

Definition for major and subclasses of serum lipoproteines and within-day precision (n = 5) for measurement of their choletserol levels.

| component peak No | particle diameter (nm) | major or subclass name | Pool 1 (mg/dl) Mean | SD | CV % | Pool 2 (mg/dl) Mean | SD | CV % |
|---|---|---|---|---|---|---|---|---|
| 1 | >90 |  | N.A. | N.A. | N.A. | 3.69 | 0.04 | 1.03 |
| 2 | 75 |  | N.A. | N.A. | N.A. | 2.06 | 0.06 | 3.13 |
| 3 | 64 | large VLDL | 0.06 | 0.01 | 20.69 | 1.95 | 0.04 | 2.30 |
| 4 | 53.6 | large VLDL | 1.16 | 0.04 | 3.07 | 1.65 | 0.06 | 3.86 |
| 5 | 44.5 | large VLDL | 2.37 | 0.09 | 3.76 | 7.58 | 0.24 | 3.14 |
| 6 | 36.8 | medium VLDL | 9.78 | 0.12 | 1.27 | 16.12 | 0.29 | 1.83 |
| 7 | 31.3 | small VLDL | 7.45 | 0.31 | 4.21 | 12.71 | 0.23 | 1.78 |
| 8 | 28.6 | large LDL | 27.92 | 0.98 | 3.51 | 18.56 | 0.46 | 2.46 |
| 9 | 25.5 | medium LDL | 38.95 | 0.14 | 0.37 | 23.28 | 0.23 | 0.97 |
| 10 | 23.0 | small LDL | 19.22 | 0.30 | 1.54 | 18.60 | 0.58 | 3.09 |
| 11 | 20.7 | very small LDL | 4.90 | 0.05 | 1.06 | 9.76 | 0.28 | 2.91 |
| 12 | 18.6 | very small LDL | 1.39 | 0.02 | 1.69 | 3.52 | 0.16 | 4.41 |
| 13 | 16.7 | very small LDL | 0.27 | 0.01 | 4.22 | 1.29 | 0.05 | 3.91 |
| 14 | 15.0 | very large HDL | 0.95 | 0.03 | 2.64 | 1.20 | 0.05 | 4.25 |
| 15 | 13.5 | very large HDL | 1.49 | 0.06 | 4.02 | 2.07 | 0.08 | 3.98 |
| 16 | 12.1 | large HDL | 20.27 | 0.68 | 3.35 | 11.51 | 0.27 | 2.37 |
| 17 | 10.9 | medium HDL | 24.64 | 0.27 | 1.09 | 14.30 | 0.20 | 1.38 |
| 18 | 9.8 | small HDL | 11.92 | 0.36 | 3.05 | 8.86 | 0.15 | 1.73 |
| 19 | 8.8 | very small HDL | 3.03 | 0.09 | 3.02 | 2.59 | 0.09 | 3.47 |
| 20 | 7.6 | very small HDL | 1.25 | 0.03 | 2.03 | 1.68 | 0.07 | 3.94 |
| 1-20 |  | total | 177.0 | 1.13 | 0.64 | 163.0 | 0.66 | 0.41 |
| 1-2 | >80 | CM | N.A. | N.A. | N.A. | 5.75 | 0.10 | 1.75 |
| 3-7 | 30-80 | VLDL | 20.81 | 0.52 | 2.51 | 40.01 | 0.52 | 1.29 |
| 8-13 | 16-30 | LDL | 92.64 | 0.56 | 0.60 | 75.02 | 0.61 | 0.81 |
| 14-20 | 8-16 | HDL | 63.55 | 0.13 | 0.20 | 42.22 | 0.33 | 0.78 |

N.A indicates not available.
CV, coefficient of variation;
CM, chyromicrons
Pool 1: normolipidemic pooled serum (TG = 56 mg/dl)
Pool 2: hyperlipidemic pooled serum (TG = 428 mg/dl)

Figure 6:
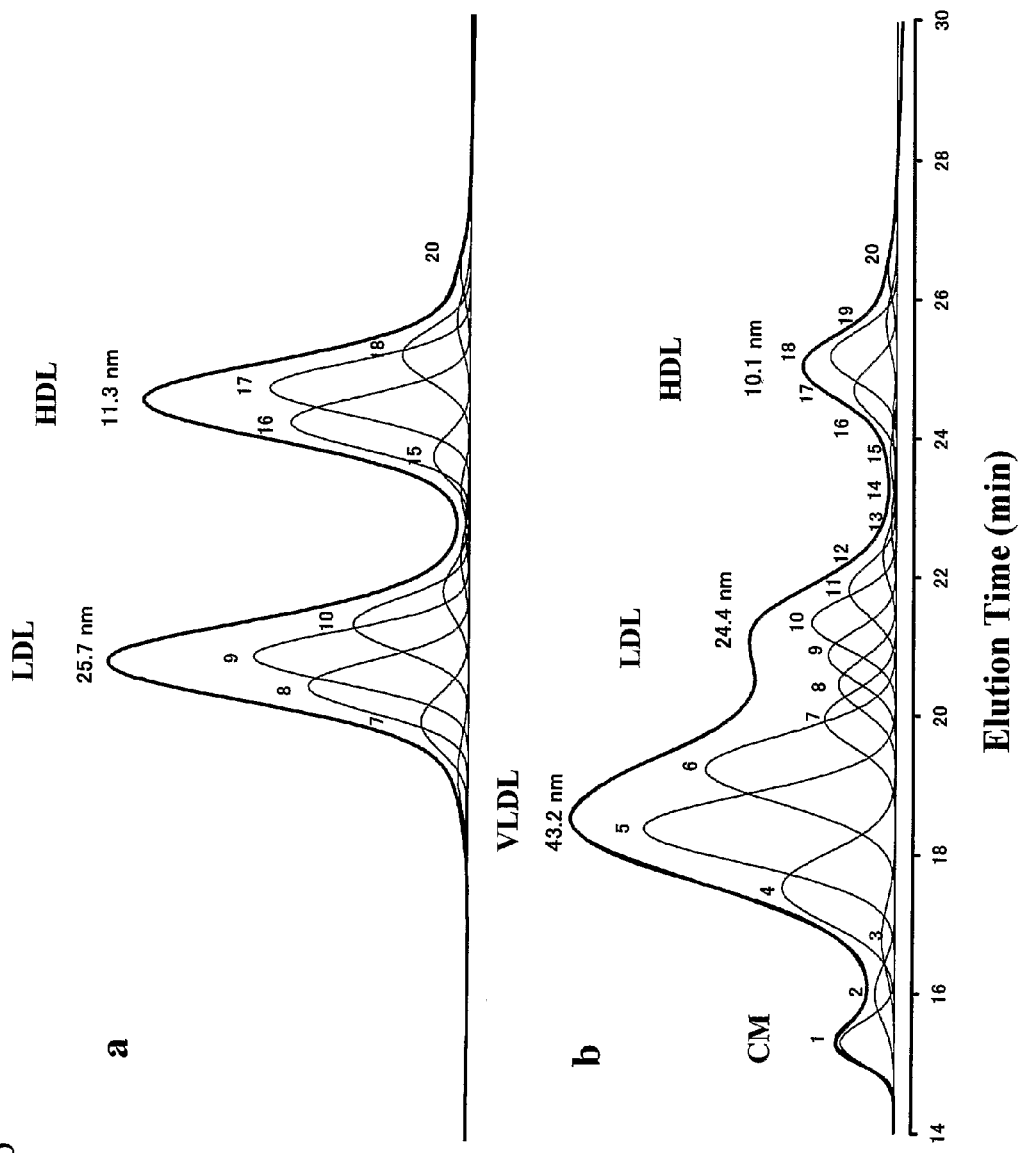
FIG. 6(a) is a profile showing a cholesterol content obtained by the use of a serum sample derived from a healthy woman, and 6(b) is a profile showing a cholesterol content obtained by the use of a serum sample derived from a patient suffering from a lipoprotein lipase deficiency.

The representative hromatograms for curve fitting analysis of normolipidemic (TC=131 mg/dL, TG=39 mg/dL) and hyperlipidemic subjects (LPL deficiency, TC=219 mg/dL, TG=1420 mg/dL) are presented in FIG. 6.

In FIG. 6, representative HPLC patterns of (a) shows a healthy woman and (b) shows a patient with LPL deficiency. A 5-μL serum sample was injected onto 2 tandem gel permeation columns (TSKgel LipopropakXL) and eluted with TSKeluent LP-1 at a flow rate of 0.7 mL per min. Solid line is real HPLC pattern detected by online enzymatic reaction for TC reagent. Dashed lines are individual subclasses and their sum of Gaussian curves, which are determined curve fitting using Gaussian summation method. Serum TC and serum TG levels are 131 mg/dL and 39 mg/dL (a) and 219 mg/dL and 1420 mg/dL (b), respectively. Particle sizes (nm) determined from observed peak times are also presented.

Within-run reproducibility (n=5) for the cholesterol determination of 20 subclasses and major classes was determined on 2 different pooled samples (pool 1: TC=177 mg/dL, TG=56 mg/dL; pool 2: TC=163 mg/dL, TG=428 mg/dL) as shown in Table 2.

Within-run reproducibility (n=5) of LDL and HDL particle sizes was 25.20±0.07 nm (coefficient of variation [CV], 0.27%) and 11.25±0.04 nm (CV, 0.36%) for pool 1 and 25.63±0.14 nm (CV, 0.56%) and 11.03±0.05 nm (CV, 0.45%) for pool 2, respectively.

Sum area of the 20 Gaussian curves was 100.2±0.4% (99.1 to 101.7%, n=62) of the area under the original chromatogram. Sum of the peak area corresponding to HDL (peaks 14 to 20) was 99.7±1.1% (98.3 to 103.9%, n=62) of the HDL peak area under the original chromatogram.

A good correlation between HDL-C determined by the precipitation method (x) and total HDL (all HDL subclasses) by HPLC (y) was obtained: y=0.975x+5.29 (r=0.973, n=62, P<0.0001). Moreover, a good correlation between LDL-C calculated by Friedewald equation (x) and total LDL (all LDL subclasses) by HPLC (y) was also obtained: y=0.903x+6.28 (r=0.977, n=62, P<0.0001).

Correlation of Cholesterol Profiles by HPLC With Clinical Parameters

Simple correlations of cholesterol levels in major lipoproteins and their subclasses with various clinical parameters (age, BMI, VFA, SFA, UA, IRI, and PAI-1) and serum TG levels are summarized in Table 3. Moreover, the correlations of LDL and IDL particle sizes are also presented in Table 3.

TABLE 3

Simple correlations of cholesterol profiles by HPLC method with clinical parameters. (n = 62)

| Clinical parameters | AGE | BMI | VFA | SFA | UA | IRI | PAI-1 | TG |
|---|---|---|---|---|---|---|---|---|
| total VLDL | 0.1001 | 0.2077 | 0.5080† | 0.0548 | 0.3676‡ | 0.2834§ | 0.1707 | 0.9428† |
| large VLDL | 0.0132 | 0.2453 | 0.4051‡ | 0.1197 | 0.2419 | 0.1848 | 0.2243 | 0.9298† |
| medium VLDL | 0.1257 | 0.2098 | 0.4883† | 0.0658 | 0.3850‡ | 0.2535§ | 0.1918 | 0.9515† |
| small VLDL | 0.1195 | 0.0695 | 0.4338† | −0.0630 | 0.3268‡ | 0.3181§ | 0.0024 | 0.5311† |
| total LDL | 0.2286 | 0.1462 | 0.4314‡ | 0.0903 | 0.2201 | 0.3493‡ | 0.0096 | 0.0568 |

TABLE 3-continued

Simple correlations of cholesterol profiles by HPLC method with clinical parameters. (n = 62)

| Clinical parameters | AGE | BMI | VFA | SFA | UA | IRI | PAI-1 | TG |
|---|---|---|---|---|---|---|---|---|
| large LDL | 0.0794 | 0.0093 | 0.1154 | 0.0163 | 0.0825 | 0.1830 | −0.1208 | −0.3292‡ |
| medium LDL | 0.2190 | 0.1435 | 0.3857‡ | 0.0976 | 0.1903 | 0.3114§ | 0.0063 | −0.0140 |
| small LDL | 0.2432 | 0.2016 | 0.5708† | 0.1110 | 0.2678§ | 0.3803‡ | 0.1223 | 0.4060‡ |
| very small LDL | 0.2399 | 0.2188 | 0.5557† | 0.1048 | 0.2917§ | 0.3746‡ | 0.1637 | 0.5768† |
| total HDL | −0.2301 | −0.2807§ | −0.5281† | −0.1800 | −0.2693§ | −0.2955§ | 0.0915 | −0.4176† |
| very large HDL | 0.1998 | −0.1909 | −0.0948 | −0.2321 | −0.1389 | −0.1493 | −0.1795 | −0.1513 |
| large HDL | 0.0570 | −0.3344‡ | −0.4265† | −0.2118 | −0.3557‡ | −0.3848‡ | −0.2768 | −0.4003‡ |
| medium HDL | −0.3290‡ | −0.2511§ | −0.5021† | −0.1585 | −0.1819 | −0.2204 | 0.2035 | −0.3783‡ |
| small HDL | −0.3817‡ | 0.2399 | −0.0219 | 0.1448 | 0.1776 | 0.2409 | 0.6165† | 0.1261 |
| very small HDL | −0.3033§ | 0.1535 | −0.0290 | 0.2380 | 0.0313 | 0.0098 | 0.3687‡ | 0.0449 |
| LDL size* | −0.0709 | −0.2457 | −0.3891‡ | −0.1882 | −0.1585 | −0.1700 | −0.3249§ | −0.5772† |
| HDL size* | 0.1660 | −0.3712‡ | −0.3678‡ | −0.2359 | −0.3544‡ | −0.3930‡ | −0.3254§ | −0.3637‡ |

Values are Pearson correlation coefficients.
*Average particle diameters (nm) obtained from LDL and HDL peak time by HPLC.
†$P < 0.001$,
‡$P < 0.01$,
§$P < 0.05$ As for age, significant negative correlations ($P<0.01$) for medium and small HDL-C were obtained. As for BMI, significant negative correlations were observed only for HDL parameters: large HDL-C ($P<0.01$) and HDL particle size ($P<0.01$). Although no correlations were observed between SFA and all of the lipoprotein subclasses, there were significant positive correlations ($P<0.01$) of VFA with VLDL-C subclasses (large, medium, and small) and LDL-C subclasses (medium, small, and very small) and negative correlations ($P<0.01$) with large and medium HDL-C, LDL, and HDL particle sizes.

As for UA, positive correlations ($P<0.01$) for VLDL-C subclasses (medium and small) and negative correlations ($P<0.01$) for large HDL-C and HDL particle size were obtained. In the case of IRI, positive correlations ($P<0.01$) for small and very small LDL-C and negative correlations ($P<0.01$) for large HDL-C and HDL particle size were obtained. As for PAI-1, positive correlations ($P<0.01$) were observed for small HDL-C and very small HDL-C. As for serum TG levels, there were significant positive correlations ($P\_0.01$) of VFA with VLDL-C subclasses (large, medium, and small) and LDL-C subclasses (small and very small) and negative correlations ($P<0.01$) with large LDL-C, HDL-C subclasses (large and medium), LDL, and HDL particle sizes.

Influences of Traditional Lipid Parameters on the Correlation Between VFA and Lipoprotein Subclasses Among the anthropometric values in Table 3, VFA levels showed most strong correlations with lipoprotein subclasses. Therefore, influences of traditional lipid parameters on the correlation between VFA and lipoprotein subclasses were examined by adjustment for serum TG, serum TC, HDL-C, and LDL-C levels, respectively (Table 4). Positive correlations of VFA with small LDL-C and very small LDL-C remained significant ($P<0.01$) after adjustment for TG, TC, HDL-C, and LDL-C, respectively.

TABLE 4

Partial correlations of cholesterol profiles by HPLC method with VFA. (n = 62)

| controlling factor | TG | TC | HDL-C | LDL-C |
|---|---|---|---|---|
| total VLDL | 0.0086 | 0.3617‡ | 0.3626‡ | 0.4946† |
| large VLDL | −0.3008§ | 0.2775§ | 0.2526§ | 0.4270† |
| medium VLDL | −0.0841 | 0.3859‡ | 0.3358‡ | 0.5220† |
| small VLDL | 0.2571§ | 0.2269 | 0.3437‡ | 0.3239§ |
| total LDL | 0.4757† | 0.0157 | 0.3173§ | 0.1405 |
| large LDL | 0.3663‡ | −0.2593§ | 0.1551 | −0.3557‡ |
| medium LDL | 0.4659† | −0.0257 | 0.2659§ | −0.0350 |
| small LDL | 0.4578† | 0.3458‡ | 0.4033† | 0.4374† |
| very small LDL | 0.3573‡ | 0.3475‡ | 0.3889‡ | 0.4241† |
| total HDL | −0.3966‡ | −0.5135† | −0.0443 | −0.4597† |
| very large HDL | −0.0164 | −0.1258 | 0.0736 | −0.1064 |
| large HDL | −0.2738§ | −0.3476‡ | −0.0821 | −0.3372‡ |
| medium HDL | −0.3831‡ | −0.4968† | −0.0889 | −0.4446† |
| small HDL | −0.1069 | −0.1571 | 0.1340 | −0.0606 |
| very small HDL | −0.0629 | −0.0469 | 0.2918§ | 0.0435 |
| LDL size* | −0.1155 | −0.3132§ | −0.2206 | −0.3786‡ |
| HDL size* | −0.2197 | −0.2771§ | −0.0810 | −0.2781§ |

Values are Pearson partial correlation coefficients. TC, HDL-C and LDL-C are the va obtained by enzymatic method, precipitation method and Friedewald equation.
*Average particle diameters (nm) obtained from LDL and HDL peak time by HPLC.
† $P < 0.001$,
‡ $P < 0.01$,
§ $P < 0.05$ As for VLDL subclasses, simple correlation analysis showed all VLDL subclasses were positively correlated with VFA, but large VLDL and small VLDL were correlated negatively and positively with VFA, respectively, after adjustment for serum TG level. In the case of LDL subclasses, adjustment for LDL-C gave a significant negative correlation ($P<0.01$) between large LDL and VFA but removed a significant positive correlation between medium LDL and VFA.

Effects of LDL-C on the Correlations Between VFA and LDL Subclasses

The studied subjects were divided into subgroups by the median value of total LDL-C levels (sum of all LDL subclasses) into the low LDL-C (n=31, LDL-C<130 mg/dL) and high LDL-C groups (n=31, LDL-C≧130 mg/dL). In the total population (n=62), a significant positive correlation (r=0.431, $P<0.001$) between VFA and total LDL-C was obtained as presented in Table 3. There was no correlation between VFA and total LDL-C in the low LDL-C group but a significant positive correlation (r=0.546, $P<0.002$) in the high LDL-C group. Scattered plots between VFA and LDL subclasses are presented in FIG. 7.

Figure 7:
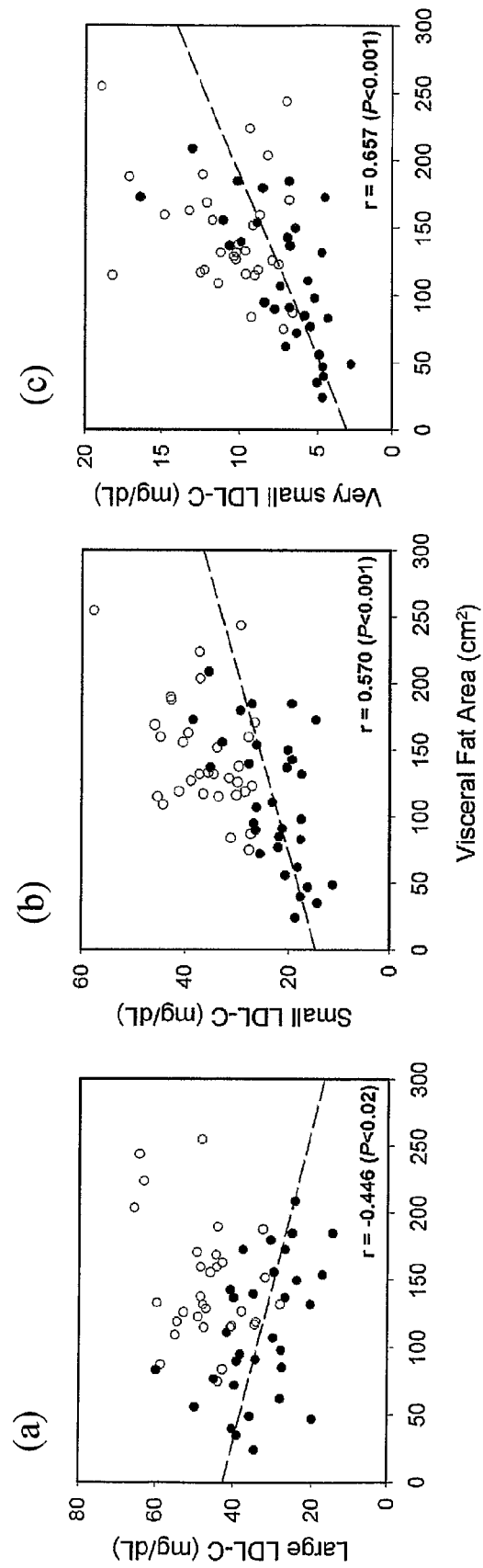
FIG. 7(a) is a scatter diagram showing a relation between a visceral fat area and a large LDL-C concentration with respect to a high LDL-C group (open circle) and a low LDL-C group (closed circle), 7(b) is a scatter diagram showing a relation between a visceral fat area and a small LDL-C concentration with respect to a high LDL-C group (open circle) and a low LDL-C group (closed circle), and 7(c) is a scatter diagram showing a relation between a visceral fat area and a very small LDL-C concentration with respect to a high LDL-C group (open circle) and a low LDL-C group (closed circle)

In FIG. 7, scatter plots of VFA against (a) large LDL-C, (b) small LDL-C, and (c) very small LDL-C for high LDL-C group (○) and low LDL-C group (●) are shown. Dashed lines represent a linear regression for low LDL-C group. Correlation coefficients and P-values are also presented for low LDL-C group (n=31).

Large LDL-C showed no significant correlations with VFA in total population and the high LDL-C group but showed a significant negative correlation (r=−0.446, P<0.02) in the low LDL-C group. Small LDL-C and very small LDL-C showed significant positive correlations with VFA in total population and both subgroups, except for very small LDL-C in high LDL-C group.

Example 2

Methods

Subjects

The 62 subjects were selected from 609 consecutive male patients who underwent cardiac catheterization in Yamagata University Hospital during two years from December 1996 to December 1998, excluding those who had received any lipid-lowering medication or those with diabetic mellitus or with any renal and liver disease. All of the subjects gave their informed consent before entering this example according to the Yamagata University Hospital ethics committees.

The selected subjects aged 62±9 years (range, 41-76 years) were separated into two groups based on the presence of CAD. In the patient group with CAD (n=45), 21 patients had a history of myocardial infarction (MI) (acute MI, 3; MI within 1 month, 11; old MI, 7), 7 patients had effort angina pectoris, 11 patients had vasospastic angina, 4 patients had unstable angina, and 2 patients did not have cardiac symptoms with significant coronary stenosis (silent myocardial ischemia). In the control subjects without CAD (n=17), 4 patients had atypical chest pain, 6 patients had cardiomyopathy, 4 patients had aortic valve disease, and 3 patients had electrocardiogram abnormality.

In this example, the following 5 rank scale from −1 to 3 in order to evaluate severity of vessel disease were defined; −1, no vessel disease; 0, vessel disease with stenosis<75%, 1, single vessel disease with stenosis≧75%; 2, double vessel disease with stenosis≧75%; 3, triple vessel disease with stenosis≧75%.

Venous blood was drawn after an overnight fasting. Plasma samples were kept in a refrigerator and analyzed within 7 days after blood collection.

HPLC Method

Plasma lipoproteins were analyzed according to the method as described in Example 1.

Other Clinical and Lipid Parameter Analysis

Plasma TG was determined enzymatically using commercial kits (Kyowa Medex, Tokyo Japan). Plasma apolipoproteins A-I, A-II, B, C-II, C-III, and E levels were determined by immunoturbidometric methods from Daiichi Chemicals, Tokyo, Japan. Fasting blood sugar (FBS) was measured by the enzymatic method. Medical records and questionnaires were used to obtain data on age, weight, height, smoking history, family history, hypertension, previous MI, angina pectoris, diabetes mellitus, and medication use. Body mass index (BMI) was calculated from weight and height as weight (kg) per [height (m)]$^2$.

Statistical Analysis:

Data are expressed as mean±SD, unless stated otherwise. Student's t test was used for determining the statistical significance of difference between groups. Correlations between various variables are presented as the Pearson's correlation coefficient (r value) and a P value<0.05 was considered to be statistically different.

Results

Comparison of Clinical Characterstics Lipid and Lipoprotein Levels

Clinical characteristics, lipid and apolipoprotein levels in 62 men in this study are shown in Table 5. As for age, BMI, FBS, percentage distribution of risk markers (current smoker, hypertension and family history), plasma TC and TG levels, there was no significant difference between the patient and the control groups. As for apolipoprotein profiles, significantly higher apolipoprotein B (P<0.05) and apolipoprotein E (P<0.01) were obtained in the patient group.

TABLE 5

| Variables | all subjects mean ± SD | min/max | patients mean ± SD | control subjects mean ± SD |
|---|---|---|---|---|
| AGE (years) | 62.4 ± 9.0 | 41/76 | 63.7 ± 8.7 | 58.8 ± 9.1 |
| BMI (kg/m$^2$) | 23.3 ± 3.1 | 16/31 | 23.6 ± 3.1 | 22.4 ± 2.9 |
| FBS (mg/dl) | 97.3 ± 15.5 | 60/128 | 98.6 ± 16.2 | 93.8 ± 13.1 |
| Current smoker | 28 (48.3%) | | 23 (51.1%) | 5 (29.4%) |
| Hypertension | 31 (50.0%) | | 21 (46.7%) | 10 (58.8%) |
| Family history | 21 (35.6%) | | 14 (31.13%) | 7 (41.1%) |
| Plasma TG (mg/dl) | 98.7 ± 51.1 | 21/241 | 103.8 ± 51.4 | 84.9 ± 48.9 |
| Plasma TC (mg/dl) | 188.3 ± 36.3 | 98/265 | 193.1 ± 36.6 | 175.8 ± 33.1 |
| Apo A-I (mg/dl) | 111.1 ± 18.2 | 72/158 | 108.7 ± 18.1 | 117.6 ± 17.3 |
| Apo A-II (mg/dl) | 25.9 ± 5.2 | 14/38 | 25.6 ± 4.9 | 26.5 ± 6.0 |
| Apo B (mg/dl) | 103.5 ± 25.2 | 41/170 | 107.6 ± 23.7 § | 92.9 ± 26.5 |
| Apo CII (mg/dl) | 3.0 ± 1.6 | 0.2/6.1 | 3.0 ± 1.5 | 2.8 ± 1.9 |
| Apo CIII (mg/dl) | 7.9 ± 2.2 | 2.3/13.8 | 8.1 ± 2.0 | 7.5 ± 2.6 |
| Apo E (mg/dl) | 4.0 ± 1.1 | 1.6/6.4 | 4.3 ± 1.1 ‡ | 3.3 ± 1.1 |

‡ P < 0.01,
§ P < 0.05 (vs control subjects),
Data represent mean value ± SD or number (%) of subjects.

We determined cholesterol levels in 3 VLDL subclasses (large, medium and small), 4 LDL subclasses (large, medium, small, and very small), 5 HDL subclasses (very large, large, medium, small and very small) by component analysis after HPLC as well as those in major lipoproteins (total VLDL, total LDL and total HDL). Table 6 compares the cholesterol levels in major lipoproteins and their subclasses of the patient group to those of the control group.

TABLE 6

| cholestsrol levels in major and subclasses (mg/dl) | patients mean ± SD | control subjects mean ± SD |
|---|---|---|
| total VLDL | 27.9 ± 11.2 | 22.4 ± 12.7 |
| large VLDL | 4.3 ± 3.6 | 4.0 ± 4.0 |

TABLE 6-continued

| cholestsrol levels in major and subclasses (mg/dl) | patients mean ± SD | control subjects mean ± SD |
|---|---|---|
| medium VLDL | 11.1 ± 6.0 | 9.6 ± 5.9 |
| small VLDL (Vs) | 12.5 ± 3.8 † | 8.7 ± 3.5 |
| total LDL | 121.7 ± 29.6 § | 103.2 ± 24.9 |
| large LDL | 34.0 ± 10.9 | 29.7 ± 8.3 |
| medium LDL | 48.9 ± 12.0 | 42.6 ± 9.9 |
| small LDL (Ls) | 28.6 ± 9.7 § | 23.4 ± 6.2 |
| very small LDL (Ls) | 10.2 ± 3.9 † | 7.5 ± 1.8 |
| total HDL | 43.4 ± 10.0 § | 50.1 ± 10.0 |
| very large HDL | 2.7 ± 1.3 | 3.1 ± 1.5 |
| large HDL (Hs) | 8.4 ± 5.2 † | 14.6 ± 8.3 |
| medium HDL | 15.9 ± 4.4 | 16.8 ± 4.4 |
| small HDL | 11.8 ± 3.1 | 11.2 ± 3.7 |
| very small HDL | 4.6 ± 1.2 | 4.3 ± 1.0 |
| non HDL-C | 149.6 ± 34.1 § | 125.7 ± 34.7 |
| TC/HDL-C | 4.6 ± 1.1 ‡ | 3.7 ± 1.1 |
| LDL-C/HDL-C | 2.9 ± 0.8 ‡ | 2.2 ± 0.8 |
| Vs + Ls − Hs | 42.9 ± 16.7 † | 25.1 ± 16.8 |
| Vs + Ls | 51.3 ± 14.5 ‡ | 39.6 ± 10.2 |
| Ls | 38.8 ± 13.4 ‡ | 30.9 ± 7.9 |
| (Vs + Ls)/Hs | 9.5 ± 6.9 ‡ | 4.2 ± 3.4 |
| Ls/Hs | 7.3 ± 5.7 ‡ | 3.2 ± 2.6 |

† $P < 0.001$,
‡ $P < 0.01$,
§ $P < 0.05$

As for major lipoprotein classes, the patient group had a significantly ($P<0.05$) higher total LDL-C and lower total HDL-C, but there was no difference in total VLDL-C levels. As for lipoprotein subclasses, the patient group had significant increases in small VLDL-C ($P<0.001$), small LDL-C ($P<0.05$), and very small LDL-C ($P<0.001$), but a significant decrease in large HDL-C ($P<0.001$). All traditional risk markers, non HDL-C, the ratios of TC/HDL-C and LDL-C/HDL-C were significantly higher in the patient group than the control group.

In order to more clearly discriminate the two groups, several derived variables were calculated from each subclass. Three subclasses (small VLDL, small LDL, and very small LDL), which were significantly increased in the patient group, were combined and expressed as "Vs+Ls". "Vs" represents a cholesterol level in small VLDL. "Ls" represents sum of a cholesterol levels in small LDL and very small LDL. The difference or the ratio of increased subclasses (Vs+Ls) and a decreased subclass (large HDL) was expressed as "Vs+Ls−Hs", and "(Vs+Ls)/Hs" or "Ls/Hs", respectively. "Hs" represents a cholesterol level in large HDL.

All these derived variables were also significantly higher in the patient group than the control group, and "Vs+Ls−Hs" showed a strongest difference.

Correlation of Cholesterol Levels in Major Lipoproteins Their Subclasses and Derived Variables with Vessel Disease Score Simple correlations of cholesterol levels in major lipoproteins and their subclasses with VD score, which is an index for CAD, are shown in Table 7. VD score was strongly and positively correlated with small VLDL-C and small LDL-C ($P<0.01$), and negatively with large HDL-C ($P<0.01$).

TABLE 7

| Controlling factors | before controlling | TG | TC | HDL-C | LDL-C | apo B | non HDL-C | TC/HDL-C | LDL-C/HDL-C |
|---|---|---|---|---|---|---|---|---|---|
| total VLDL | 0.157 | 0.131 | 0.087 | 0.073 | 0.080 | −0.010 | 0.008 | −0.128 | −0.036 |
| large VLDL | 0.067 | −0.037 | 0.012 | −0.018 | 0.021 | −0.061 | −0.046 | −0.160 | −0.080 |
| medium VLDL | 0.035 | −0.099 | −0.030 | −0.071 | −0.019 | −0.128 | −0.101 | −0.263§ | −0.152 |
| small VLDL (Vs) | 0.341‡ | 0.329‡ | 0.317§ | 0.312§ | 0.271§ | 0.254§ | 0.259§ | 0.184 | 0.203 |
| total LDL | 0.217 | 0.200 | 0.218 | 0.235 | — | 0.022 | −0.008 | 0.028 | −0.019 |
| large LDL | −0.001 | −0.010 | −0.185 | 0.039 | −0.263§ | −0.234 | −0.247 | −0.138 | −0.154 |
| medium LDL | 0.188 | 0.171 | 0.114 | 0.218 | −0.142 | −0.021 | −0.068 | 0.017 | −0.031 |
| small LDL (Ls) | 0.338‡ | 0.324§ | 0.335‡ | 0.326§ | 0.294§ | 0.250§ | 0.260§ | 0.186 | 0.154 |
| very small LDL (Ls) | 0.300§ | 0.285§ | 0.261§ | 0.273§ | 0.212 | 0.203 | 0.201 | 0.143 | 0.108 |
| total HDL | −0.241 | −0.220 | −0.282§ | — | −0.257§ | −0.217 | −0.228 | 0.022 | −0.010 |
| very large HDL | −0.224 | −0.203 | −0.236 | −0.103 | −0.222 | −0.207 | −0.204 | −0.075 | −0.085 |
| large HDL (Hs) | −0.344‡ | −0.337‡ | −0.328‡ | −0.257§ | −0.304§ | −0.284§ | −0.285§ | −0.144 | −0.152 |
| medium HDL | −0.090 | −0.055 | −0.134 | 0.210 | −0.123 | −0.082 | −0.093 | 0.163 | 0.126 |
| small HDL | 0.115 | 0.093 | 0.045 | 0.144 | 0.021 | 0.029 | 0.011 | 0.057 | 0.045 |
| very small HDL | 0.124 | 0.119 | 0.078 | 0.207 | 0.074 | 0.087 | 0.071 | 0.146 | 0.141 |
| Vs + Ls − Hs | 0.428† | 0.430† | 0.447† | 0.373‡ | 0.427† | 0.397‡ | 0.428† | 0.268§ | 0.266§ |
| Vs + Ls | 0.387‡ | 0.377‡ | 0.450† | 0.365‡ | 0.424‡ | 0.343‡ | 0.389‡ | 0.226 | 0.209 |
| Ls | 0.333‡ | 0.319§ | 0.320§ | 0.317§ | 0.278§ | 0.242 | 0.250 | 0.178 | 0.145 |
| (Vs + Ls)/Hs | 0.343‡ | 0.331‡ | 0.323§ | 0.256§ | 0.294§ | 0.292§ | 0.285§ | 0.161 | 0.152 |
| Ls/Hs | 0.335‡ | 0.321§ | 0.314§ | 0.248 | 0.284§ | 0.286§ | 0.277§ | 0.160 | 0.144 |

Values are Pearson correlation coefficients.

[a] VD score: Vessel Disease score, −1, no vessel disease; 0, vessel disease with stenosis <75%, 1, single vessel disease with stenosis ≧75%; 2, double vessel disease with stenosis ≧75%; 3, triple vessel disease with stenosis ≧75%.

† $P < 0.001$,
‡ $P < 0.01$,
§ $P < 0.05$

We also examined the correlations between VD score and several derived variables as presented in Table 6. As shown in Table 7, all variables had strong positive correlations higher than r=0.333 (n=62, P<0.01) with VD score, and the strongest correlation (r=0.428, P<0.001) was obtained for "Vs+Ls–Hs". As for traditional lipid risk markers, VD score was significantly (P<0.01) correlated with the LDL-C/HDL-C and the TC/HDL-C ratios but not with non HDL-C (results not shown).

Influences of Traditional Lipid Parameters on the Correlation of CAD Severity with Lipoprotein Subclasses and Their Derived Variables The influences of traditional lipid parameters on the correlation between VD score, lipoprotein subclasses and their derived variables were examined in order to evaluate clinical usefulness of these variables for the relevance of CAD severity. Table 7 shows the partial correlation coefficients between HPLC variables and VD score after controlling for each traditional single variable (TG, TC, HDL-C, LDL-C and apolipoprotein B) or each combination variable such as non HDL-C, TC/BDL-C and LDL-C/HDL-C. Controlling for plasma TG, TC and HDL-C did not give so much influence on the correlation between VD score and the HPLC variables. On the other hand, a positive correlation of very small LDL-C with VD score became nonsignificant after controlling for LDL-C, apolipoprotein B or non HDL-C. A significant negative correlation of large LDL-C with VD score was produced after adjustment for LDL-C. Controlling for TC/HDL-C or LDL-C/BDL-C removed all significant correlations, but a negative correlation of medium VLDL-C with VD score became significant after controlling for TC/HDL-C. Positive correlations of "Vs+Ls–Hs" with VD score remained significant even after controlling for any factor. Moreover, significant positive correlations of "Vs+Ls" with VD score remained except for controlling for TC/HDL-C or LDL-C/HDL-C.

Example 3

In this example, 59 samples shown in Table 8 were analyzed by using a Superose 6BR 10/30 column (produced by Pharmacia) and two TSKgel LipopropakXL columns (produced by Tosoh Corp.), and then the obtained results were compared to each other.

TABLE 8

| | mean SD | min max |
|---|---|---|
| AGE (years) | 41.4 ± 9.8 | (25.0~57.1) |
| BMI (kg/m$^2$) | 23.4 ± 2.8 | (19.1~31.8) |
| TC (mg/dl) | 205.6 ± 35.7 | (134.0~295.0) |
| TG (mg/dl) | 134.1 ± 80.3 | (42.0~421.0) |
| Apo A-I (mg/dl) | 150.9 ± 26.6 | (99.0~238.0) |
| Apo A-II (mg/dl) | 32.4 ± 5.5 | (23.2~49.7) |
| Apo B (mg/dl) | 103.1 ± 28.4 | (44.0~173.0) |
| Apo C-II (mg/dl) | 4.6 ± 2.1 | (0.7~10.1) |
| Apo C-III (mg/dl) | 10.4 ± 3.3 | (5.8~19.2) |
| Apo E (mg/dl) | 4.1 ± 1.2 | (2.1~7.2) |
| Lp(a) (mg/dl) | 16.3 ± 17.7 | (2.0~99.0) |

In this example, 44 samples shown in Table 9 were further analyzed by using a SkylightPak-LDL column (produced by Skylight Biotech Inc.) and two TSKgel LipopropakXL columns (produced by Tosoh Corp.), and then the obtained results were compared to each other.

TABLE 9

| | mean ± SD | min~max |
|---|---|---|
| TC (mg/dl) | 213.9 ± 22.1 | (156.9~265.1) |
| TG (mg/dl) | 115.2 ± 82.5 | (36.2~497.9) |
| HDL-C (mg/dl) | 68.6 ± 17.2 | (41.3~113.6) |

In this example, elution times (particle sizes) of 20 component peaks were defined as shown in Table 10.

TABLE 10

| | Component peak No | | | | | | | | | |
|---|---|---|---|---|---|---|---|---|---|---|
| | 1 | 2 | 3 | 4 | 5 | 6 | 7 | 8 | 9 | 10 |
| Particle Diameter (nm) | >90 | 75 | 64 | 53.6 | 44.5 | 36.8 | 31.3 | 28.6 | 25.5 | 23.0 |
| Subclass Name | | | | large VLDL | medium VLDL | | small VLDL | large LDL | medium LDL | small LDL |
| Major Class | CM > 80 nm | | | VLDL: 30-80 nm | | | | LDL: 16-30 nm | | |

| | Component peak No | | | | | | | | | |
|---|---|---|---|---|---|---|---|---|---|---|
| | 11 | 12 | 13 | 14 | 15 | 16 | 17 | 18 | 19 | 20 |
| Particle Diameter (nm) | 20.7 | 18.6 | 16.7 | 15.0 | 13.5 | 12.1 | 10.9 | 9.8 | 8.8 | 7.6 |
| Subclass Name | very small LDL | | | very large HDL | | large HDL | medium HDL | small HDL | very small HDL | |
| Major Class | LDL: 16-30 nm | | | | | | HDL: 8-16 nm | | | |

Figure 8A:
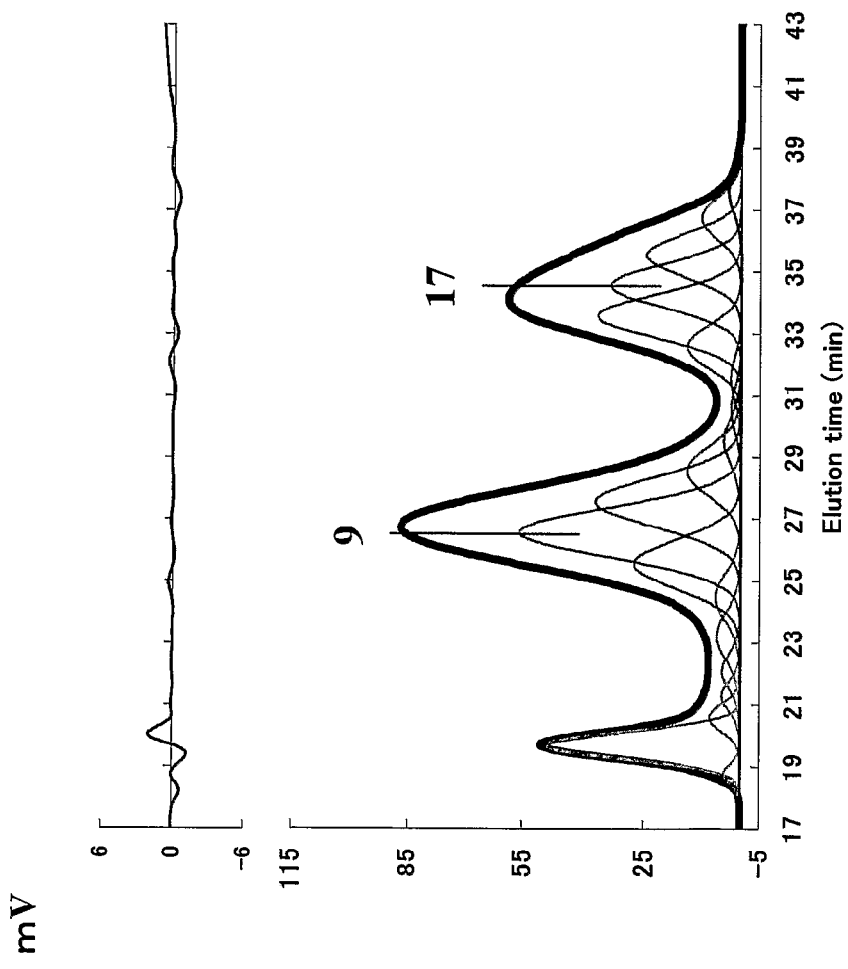
FIG. 8(a) is a characteristic diagram showing a result of analysis of cholesterol performed by using a Superose 6HR 10/30 column for a pooled serum from human healthy subjects.
Figure 8B:
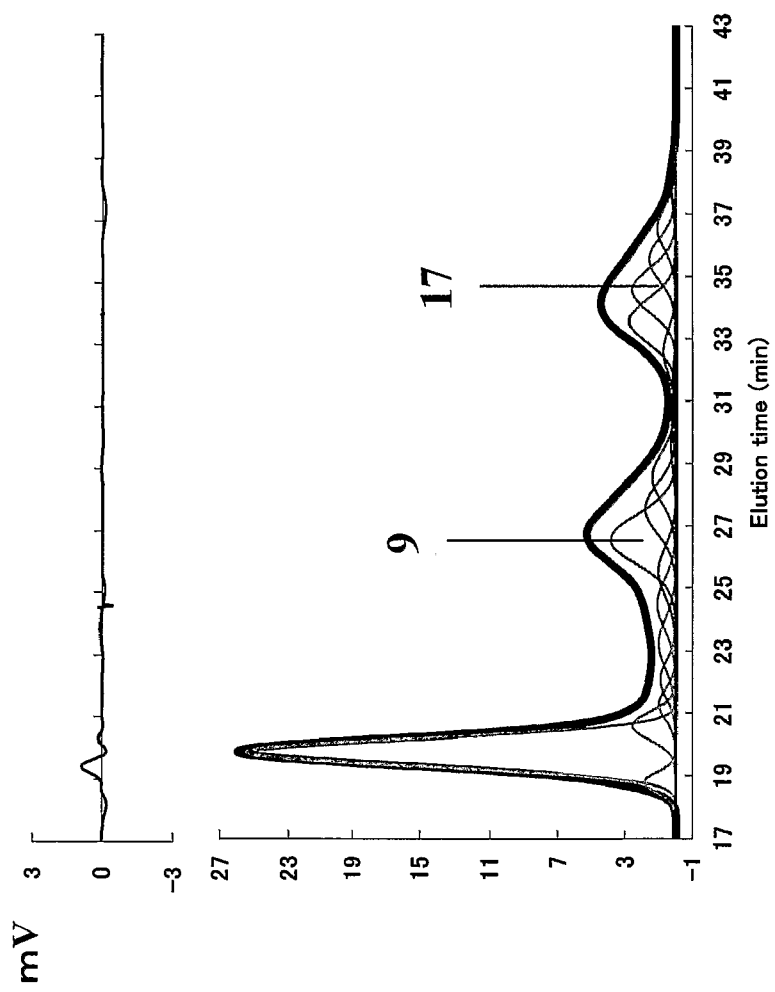
FIG. 8(b) is a characteristic diagram showing a result of analysis of triglycerides performed by using a Superose 61R 10/30 column for a pooled serum from human healthy subjects.
Figure 9A:
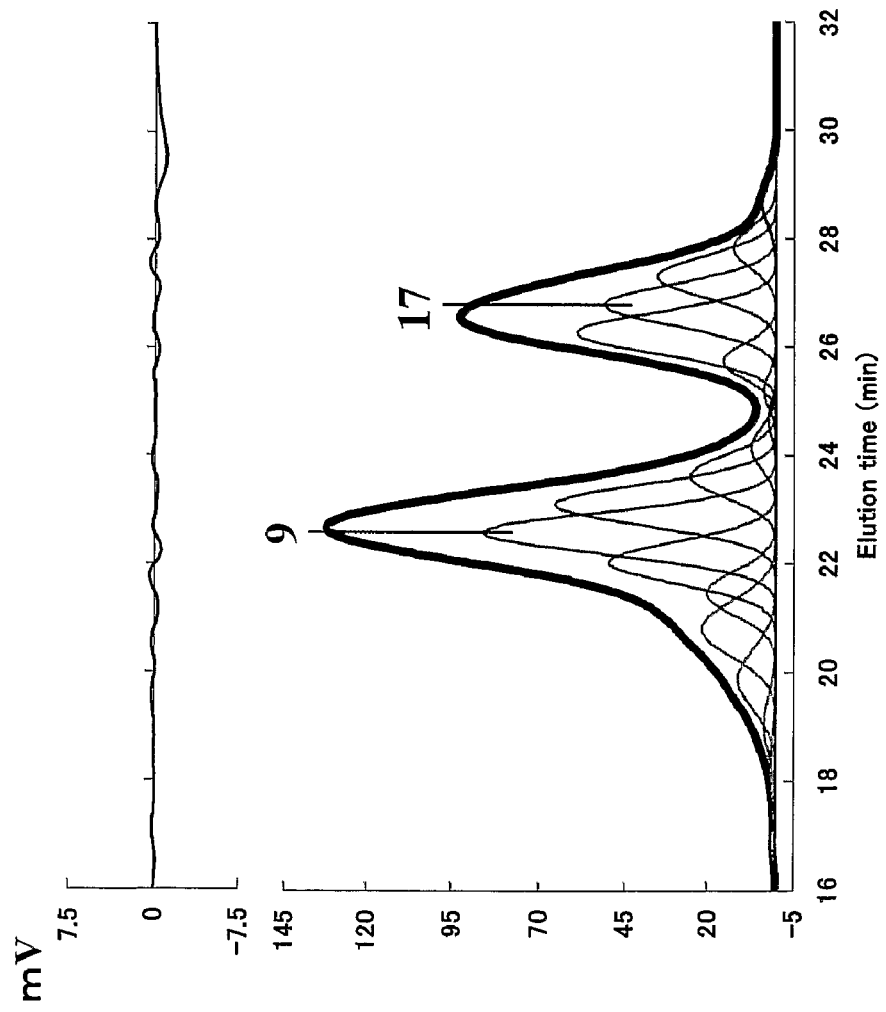
FIG. 9(a) is a characteristic diagram showing a result of analysis of cholesterol performed by using two TSKgel LipopropakXL columns for a pooled serum from human healthy subjects.
Figure 9B:
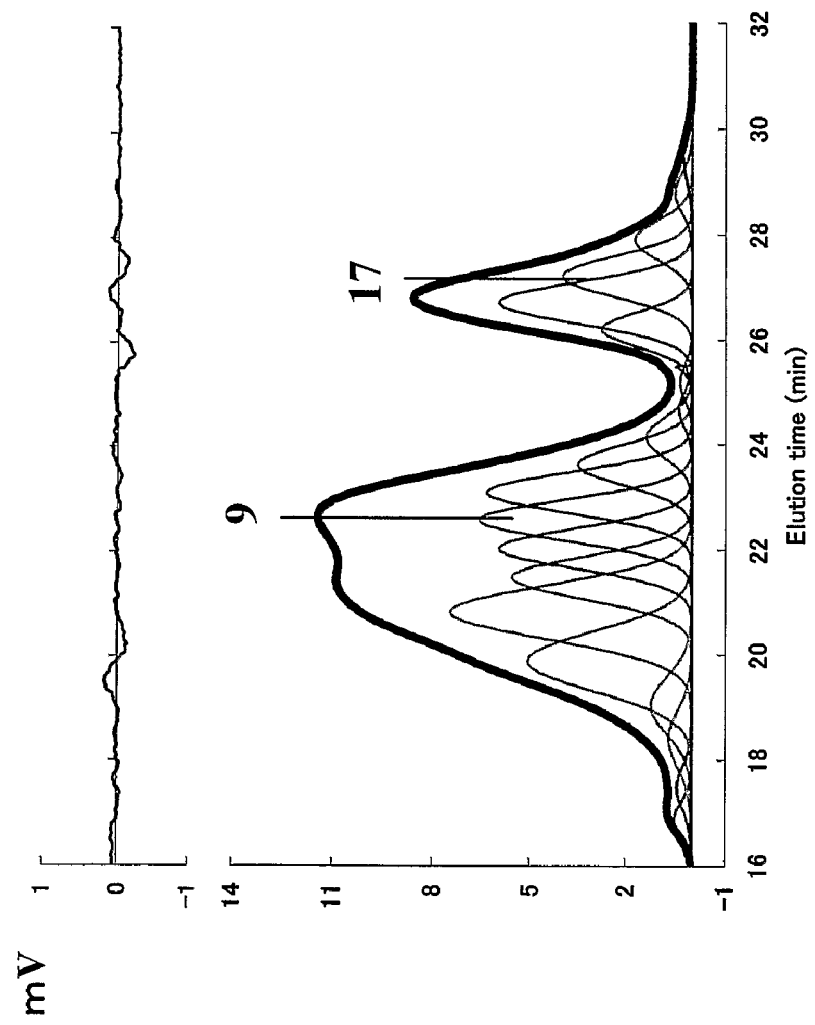
FIG. 9(b) is a characteristic diagram showing a result of analysis of triglycerides performed by using two TSKgel LipopropakXL columns for a pooled serum from human healthy subjects.
Figure 10A:
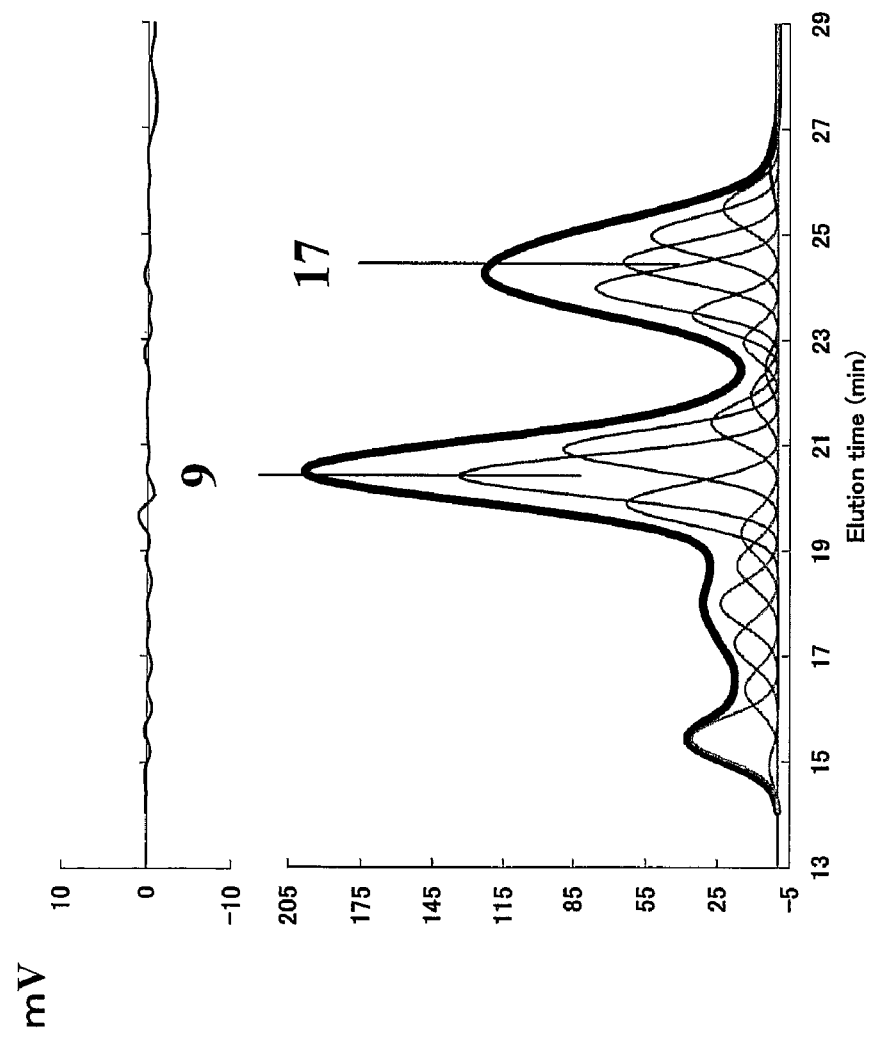
FIG. 10(a) is a characteristic diagram showing a result of analysis of cholesterol performed by using a SkylightPak-LDL column for a pooled serum from human healthy subjects.
Figure 10B:
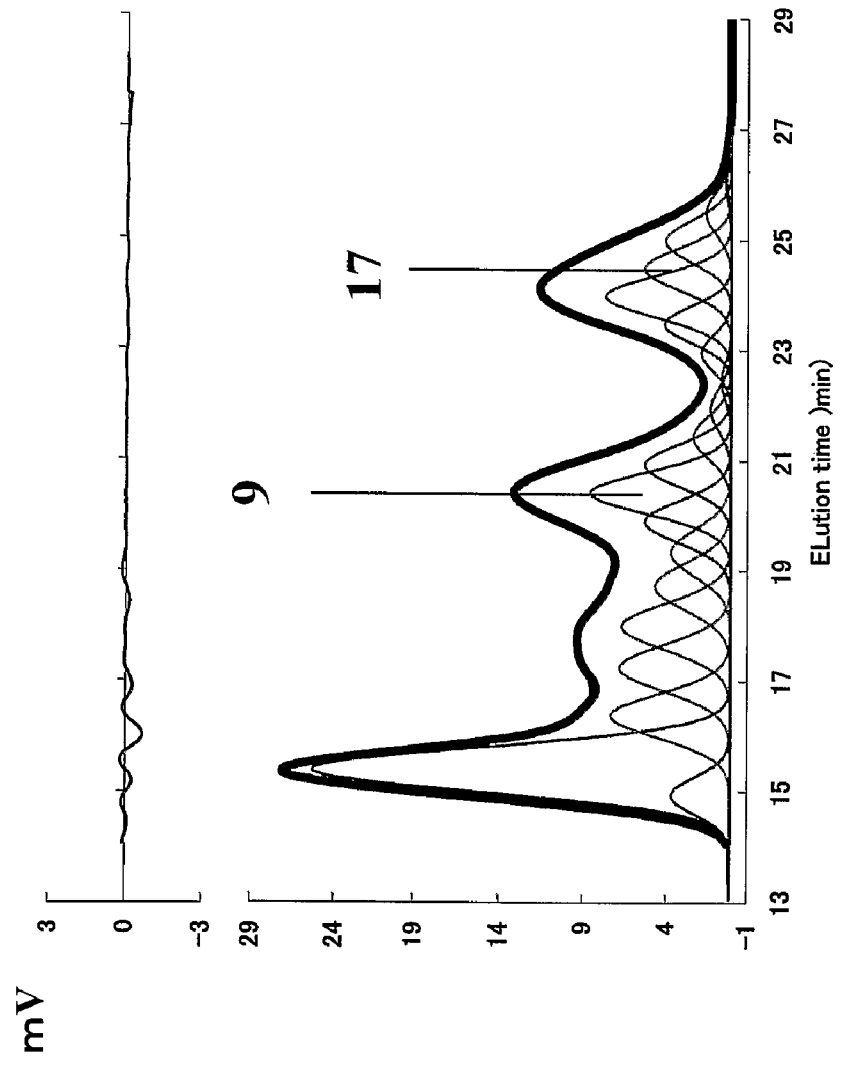
FIG. 10(b) is a characteristic diagram showing a result of analysis of triglycerides performed by using a SkylightPak-LDL column for a pooled serum from human healthy subjects.

As for a pooled serum from human healthy subjects, FIGS. 8(*a*) and (*b*) show analytical results obtained by using the Superose 6HR 10/30 column, FIGS. 9(*a*) and (*b*) show analytical results obtained by using the TSKgel LipopropakXL column and FIGS. 10(*a*) and (*b*) show analytical results obtained by using the SkylightPak-LDL column. Thick lines depicted in FIGS. 8(*a*), 9(*a*) and 10(*a*) show profiles of cholesterol before separating thereof into component peaks. Thick lines depicted in FIGS. 8(*b*), 9(*b*) and 10(*b*) show profiles of triglycerides before separating thereof into component peaks.

Figure 11:
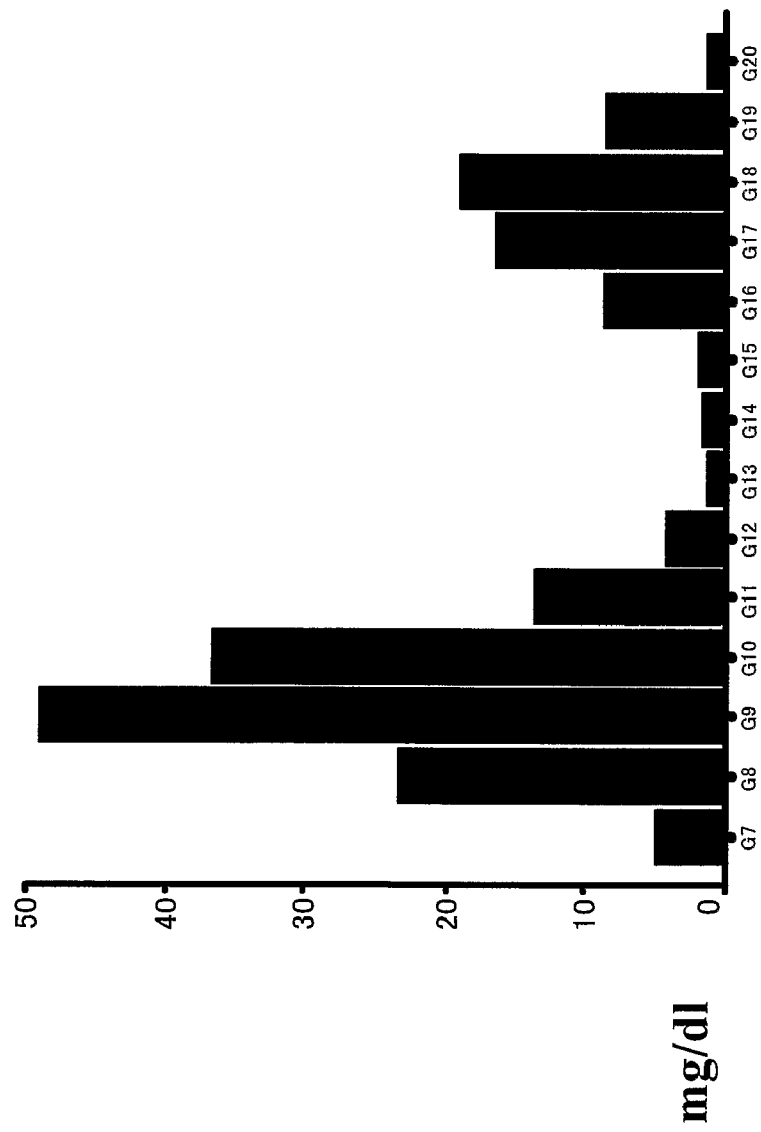
FIG. 11 is a characteristic diagram showing a calculation result of average cholesterol content at each peak of G7 to G20 which are from the result shown in FIG. 8 for 59 subjects shown in Table 8 using the Superose 6HR 10/30 column.
Figure 12:
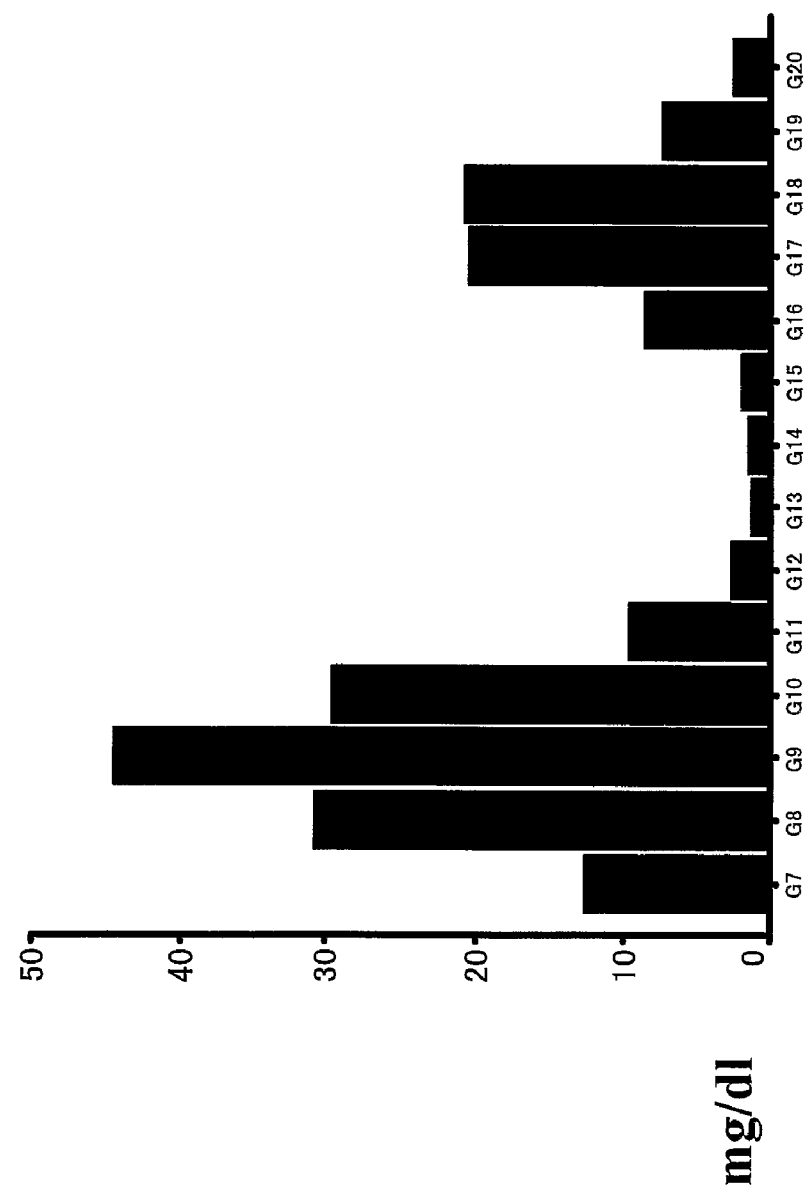
FIG. 12 is a characteristic diagram showing a calculation result of average cholesterol content at each peak of G7 to G20 which are from the result shown in FIG. 9 for 59 subjects shown in Table 8 using the TSKgel LipopropakXL column.
Figure 13:
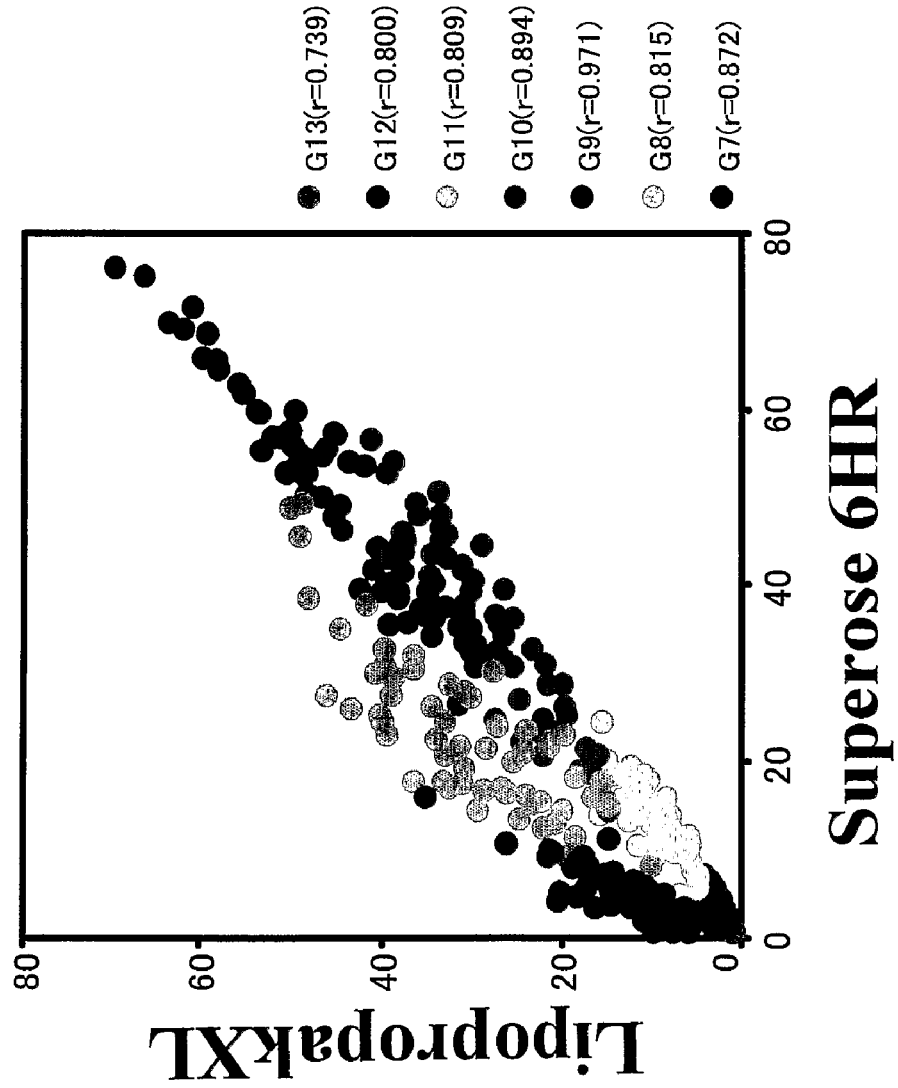
FIG. 13 is a characteristic diagram showing a result of comparison between Superose 6BR 10/30 and TSKgel LipopropakXL columns in terms of a cholesterol content at each component peak of G7 to G13 (corresponding to a range from a small VLDL subclass to a LDL subclass), based on the results shown in FIGS. 11 and 12 for 59 subjects shown in Table 8.
Figure 14:
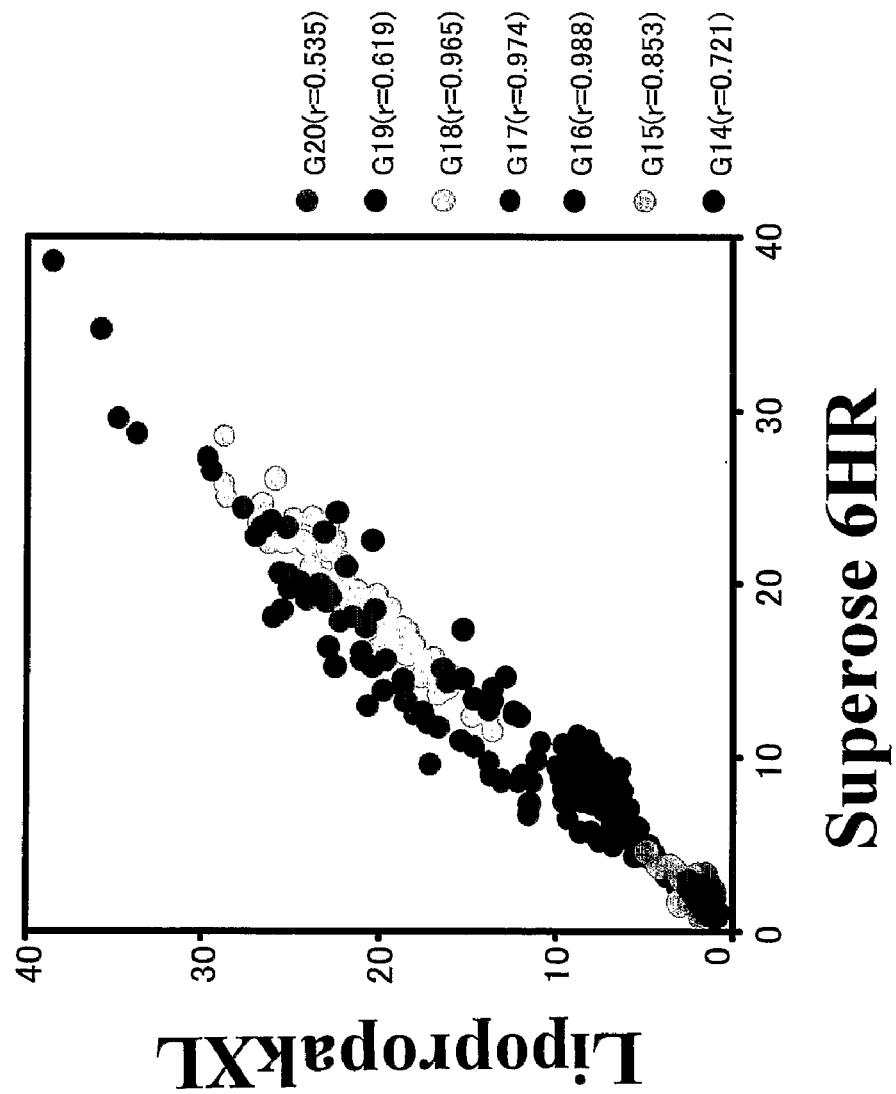
FIG. 14 is a characteristic diagram showing a result of comparison between Superose 6HR 10/30 and TSKgel LipopropakXL columns in terms of a cholesterol content at each component peak of G14 to G20 (corresponding to a HDL subclass), based on the results shown in FIGS. 11 and 12 for 59 subjects shown in Table 8.

FIG. 11 shows results of calculating average cholesterol contents included in respective peaks G7 to G20 which are from the results shown in FIG. 8(*a*) for 59 subjects shown in Table 8 using the Superose 6HR 10/30 column. And FIG. 12 shows results of calculating average cholesterol contents included in respective peaks G7 to G20 which are from the results shown in FIG. 9(*a*) for 59 subjects shown in Table 8 using the TSKgel LipopropakXL column. FIG. 13 shows a result of comparison between the Superose 6HR 10/30 and the TSKgel LipopropakXL columns in terms of cholesterol contents included in respective component peaks G7 to G13 (corresponding to small VLDL to LDL subclasses), based on the results shown in FIGS. 11 and 12 for 59 subjects shown in Table 8. Further, FIG. 14 shows a result of comparison between both columns in terms of cholesterol contents included in respective component peaks G14 to G20 (corresponding to HDL subclass), based on the results shown in FIGS. 11 and 12 for 59 subjects shown in Table 8.

As can be seen in FIGS. 8(*a*), 9(*a*), 11-14, cholesterol contents included in 14 component peaks, G7 to G20, were shown to be approximately consistent when using either the Superose 6HR 10/30 or the TSKgel LipopropakXL columns.

Figure 15:
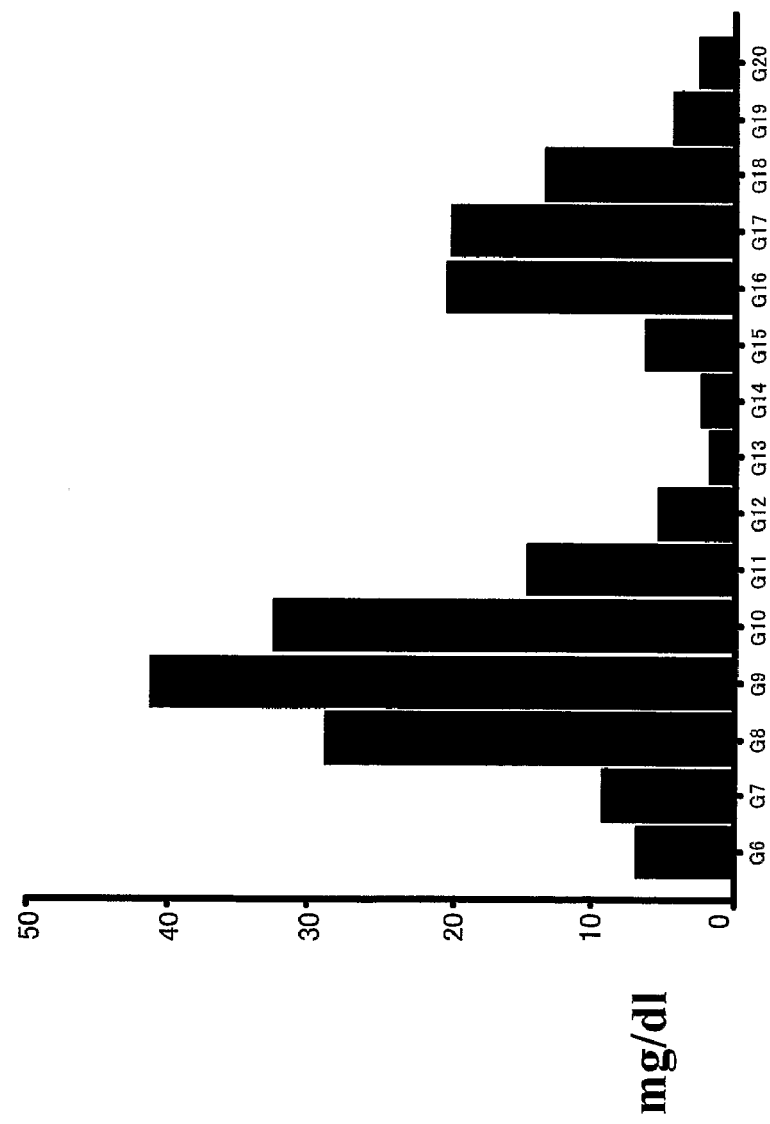
FIG. 15 is a characteristic diagram showing a calculation result of average cholesterol content at each peak of G6 to G20 which are from the result shown in FIG. 9 for 44 subjects shown in Table 9 using the TSKgel LipopropakXL column.
Figure 16:
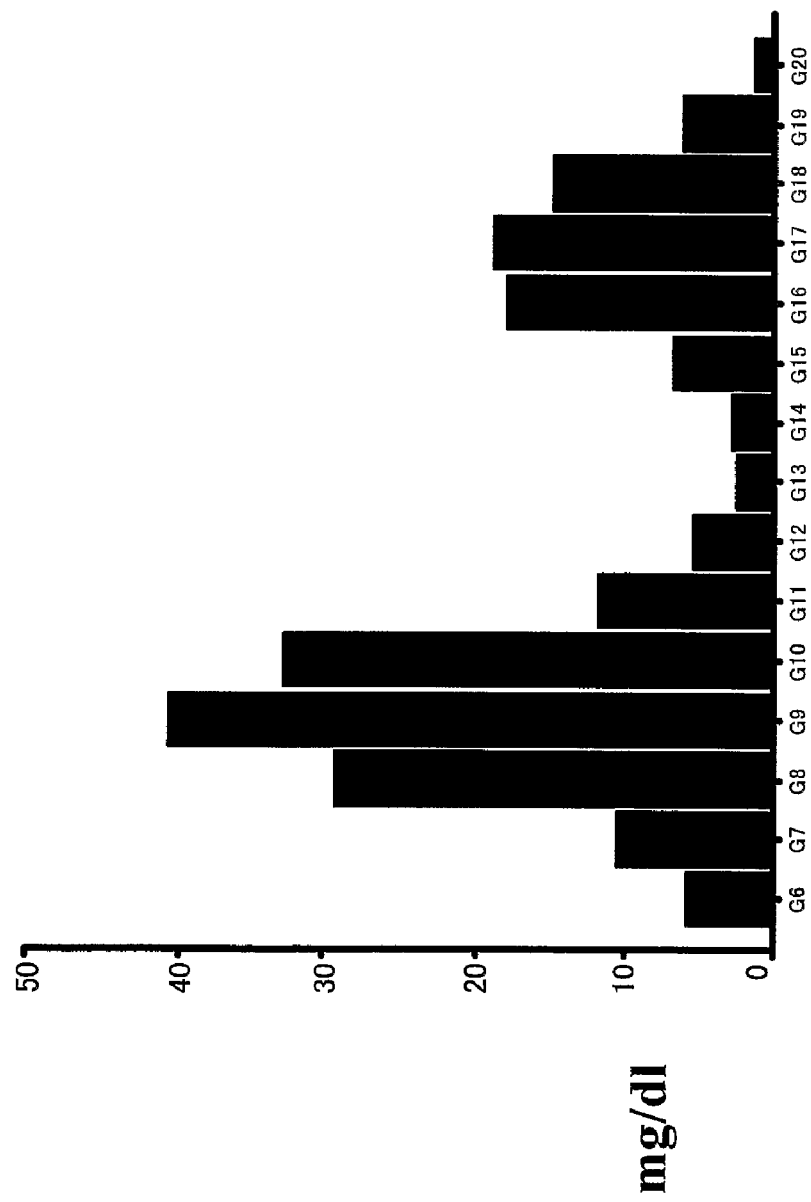
FIG. 16 is a characteristic diagram showing a calculation result of average cholesterol content at each peak of G6 to G20 which are from the result shown in FIG. 10 for 44 subjects shown in Table 9 using the SkylightPak-LDL column.
Figure 17:
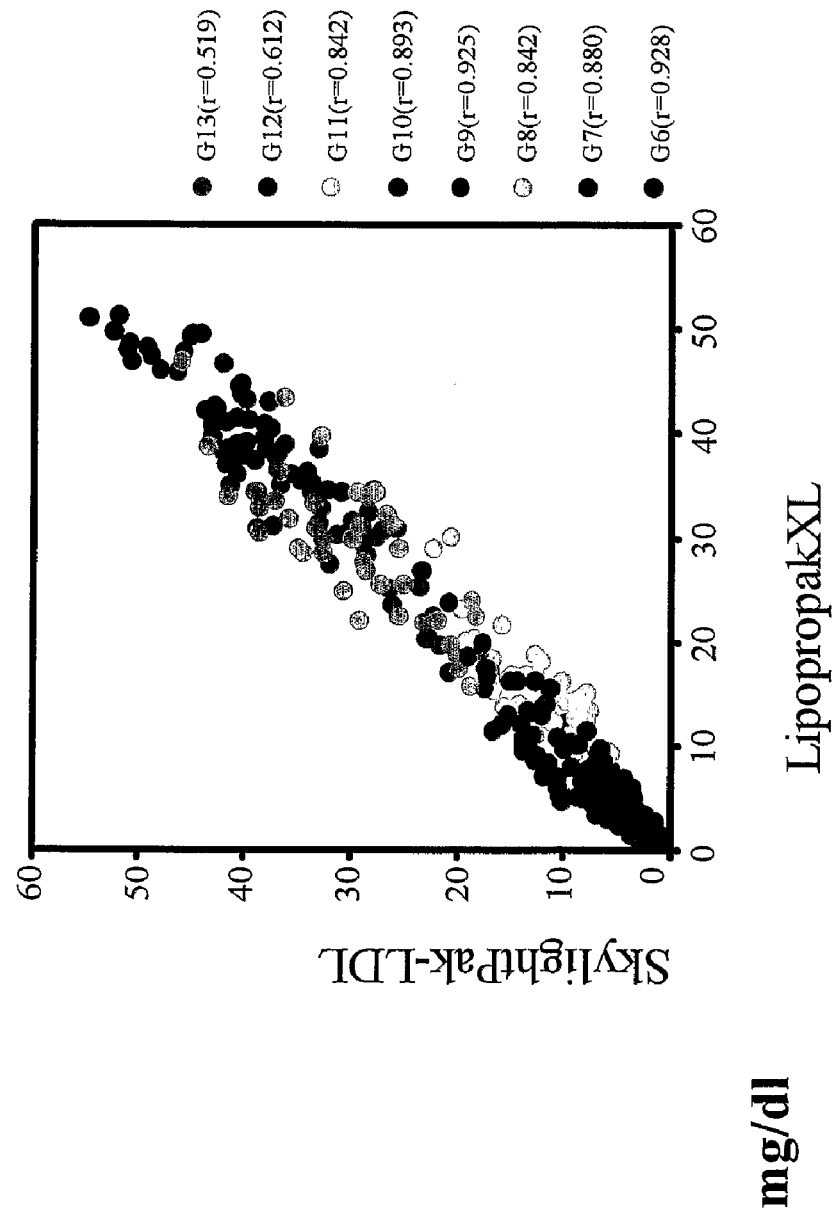
FIG. 17 is a characteristic diagram showing a result of comparison between TSKgel LipopropakXL and SkylightPak-LDL columns in terms of a cholesterol content at each component peak of G6 to G13 (corresponding to a range from a medium VLDL subclass to a LDL subclass), based on the results shown in FIGS. 15 and 16 for 44 subjects shown in Table 9.
Figure 18:
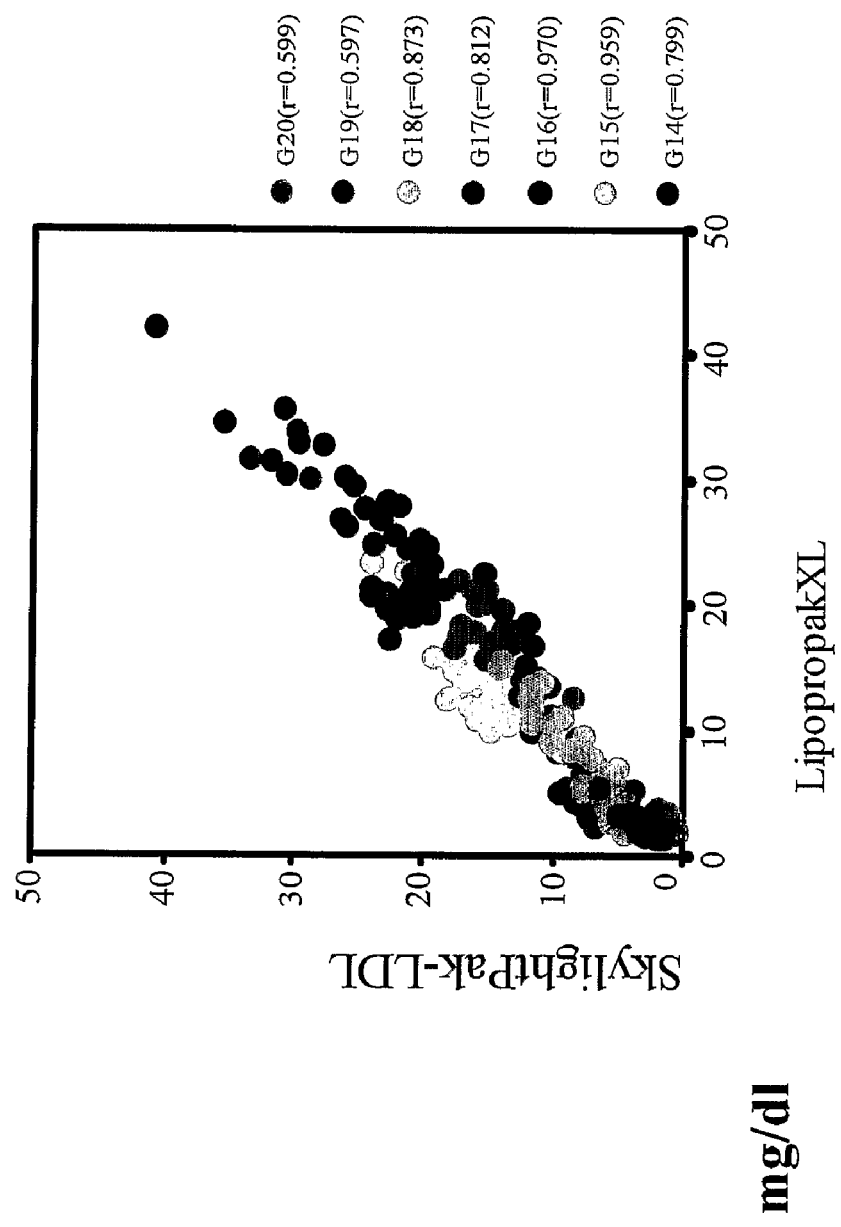
FIG. 18 is a characteristic diagram showing a result of comparison between TSKgel LipopropakXL and SkylightPak-LDL columns in terms of a cholesterol content at each component peak of G14 to G20 (corresponding to a HDL subclass), based on the results shown in FIGS. 15 and 16 for 44 subjects shown in Table 9.

FIG. 15 shows results of calculating average cholesterol contents included in respective peaks G6 to G20 among the results shown in FIG. 9(*a*) for 44 subjects shown in Table 9 using the TSKgel LipopropakXL column. And FIG. 16 shows results of calculating average cholesterol contents included in respective peaks G6 to G20 among the results shown in FIG. 10(*a*) for 44 subjects shown in Table 9 using the SkylightPak-LDL column. FIG. 17 shows a result of comparison between the TSKgel LipopropakXL and the SkylightPak-LDL columns in terms of cholesterol contents included in respective component peaks G6 to G13 (corresponding to medium VLDL to LDL subclasses), based on the results shown in FIGS. 15 and 16 for 44 subjects shown in Table 9. Further, FIG. 18 shows a result of comparison between both columns in terms of cholesterol contents included in respective component peaks G14 to G20 (corresponding to HDL subclass), based on the results shown in FIGS. 15 and 16 for 44 subjects shown in Table 9.

As can be seen in FIGS. 9(*a*), 10(*a*), 15-18, cholesterol contents included in 15 component peaks, G6 to G20, were shown to be approximately consistent when using either the TSKgel LipopropakXL or the SkylightPak-LDL columns.

Thus, according to the method of analysis of the present invention, results of data-analysis with excellent reliability can be obtained even when any column is used regardless of some characteristics such as resolution thereof. Also, as shown in FIGS. 8(*b*), 9(*b*) and 10(*b*), the method of analysis of the present invention can be applied to analysis of triglycerides similar to the analysis of cholesterol as described above. In other words, according to the method of analysis of the present invention, the component peaks that have been defined based on a detected signals derived from cholesterol, are used for calculating the approximated curve regarding a profile derived from triglycerides, free cholesterol, phospholipids, apolipoproteins and the like.

INDUSTRIAL APPLICABILITY

As has been described in detail, the present invention provides an apparatus and a method for analyzing lipoprotein particles, in which comparison can be performed between subclasses of a plurality of samples even when gel filtration columns with different resolutions or molecular size ranges are used. According to the apparatus and the method for analyzing lipoprotein particles of the present invention, it is possible to obtain data with higher reliability compared with the conventional and well-known procedures and apparatus. The data obtained by the apparatus and the method for analyzing lipoprotein particles according to the present invention can effectively be used for diagnosing various diseases caused by e.g. visceral fat accumulation such as diabetes, hypertension, hyperlipidemia, and coronary artery diseases.

The invention claimed is:

1. A method of analysis of lipoprotein particles comprising the steps of:

separating a plurality of classes of lipoproteins contained in an obtained subject sample by liquid chromatography and detecting signals of VLDL, LDL and HDL in the separated lipoprotein particles, wherein each of the lipoprotein particles is constituted of subclasses estimated from chromatogram component peaks consisting of anchor peaks and extra essential peaks, wherein the chromatogram component peaks are curves obtained by separating a chromatogram curve signal associated with said subject sample into multiple curves, and calculating an approximated curve corresponding to summation of the chromatogram component peaks using said detected signals, wherein elution position(s) of one or more anchor peak(s) of said anchor peaks are determined by elution positions observed in a metabolic disorder patient whose lipoprotein metabolism suggests that the size ranges of VLDL, LDL, and HDL are narrow.

2. The method of analysis according to claim 1, wherein said anchor peaks correspond to at least one peak selected from a peak curve for particles with a particle diameter of 44.5±2.1 nm, a peak curve for particles with a particle diameter of 36.8±2.5 nm, a peak curve for particles with a particle diameter of 31.3±1.0 nm, a peak curve for particles with a particle diameter of 25.5±0.4 nm, a peak curve for particles with a particle diameter of 23.0±0.5 nm, a peak curve for particles with a particle diameter of 13.5±0.4 nm, a peak curve for particles with a particle diameter of 10.9±0.2 nm, and a peak curve for particles with a particle diameter of 9.8±0.2 nm.

3. The method of analysis according to claim 1, wherein elution positions and peak widths of said extra essential peaks are preset so as to be located between said anchor peaks at almost equal intervals.

4. The method of analysis according to claim 1, wherein said approximated curve consists of 20 component peaks.

5. A method of diagnosis of a disease caused by accumulation of visceral fat comprising the steps of:
  providing a subject sample taken from a subject to be diagnosed;
  separating a plurality of classes of lipoproteins contained in an obtained subject sample by liquid chromatography and detecting signals of VLDL, LDL and HDL in the separated lipoprotein particles;
  assuming that each of the lipoproteins is constituted of subclasses estimated from chromatogram component peaks consisting of anchor peaks and extra essential peaks, wherein the chromatogram component peaks are curves obtained by separating a chromatogram curve signal associated with said subject sample into multiple curves;
  calculating an approximated chromatogram curve corresponding to summation of the chromatogram component peaks using said detected signals; and
  analyzing said calculated approximated chromatogram curve, wherein elution position(s) of one or more anchor peak(s) of said anchor peaks are determined by elution positions observed in a metabolic disorder patient whose lipoprotein metabolism suggests that the size ranges of VLDL, LDL, and HDL are narrow.

6. The method of diagnosis according to claim 5, wherein said anchor peaks correspond to at least one peak selected from
  a peak curve for particles with a particle diameter of 44.5±2.1 nm,
  a peak curve for particles with a particle diameter of 36.8±2.5 nm,
  a peak curve for particles with a particle diameter of 31.3±1.0 nm,
  a peak curve for particles with a particle diameter of 25.5±0.4 nm,
  a peak curve for particles with a particle diameter of 23.0±0.5 nm,
  a peak curve for particles with a particle diameter of 13.5±0.4 nm,
  a peak curve for particles with a particle diameter of 10.9±0.2 nm, and
  a peak curve for particles with a particle diameter of 9.8±0.2 nm.

7. The method of diagnosis according to claim 5, wherein elution positions and peak widths of said extra essential peaks are preset so as to be located between said anchor peaks at almost equal intervals.

8. The method of diagnosis according to claim 5, wherein said approximated curve consists of 20 component peaks.

9. The method of diagnosis according to claim 5, wherein said step of analyzing is to compare cholesterol contents in large VLDL, medium VLDL, small VLDL, medium LDL, small LDL, very small LDL, large HDL, and medium HDL with a reference value.

10. The method of diagnosis according to claim 5, wherein said step of analyzing is to diagnose a disease as arteriosclerosis by comparing the cholesterol content in the large LDL with the reference value.

11. The method of diagnosis according to claim 5, wherein said step of analyzing is to diagnose a disease as a coronary artery disease by comparing the cholesterol contents in the small VLDL, the small LDL, the very small LDL, and the large HDL with the reference value.

12. A method of diagnosis of coronary artery disease comprising the steps of:
  analyzing lipoprotein contained in a subject sample taken from a subject to be diagnosed using the method for analyzing lipoproteins according to any one of claims 1, 2, 3, and 4;
  separating a plurality of classes of lipoproteins contained in an obtained subject sample by liquid chromatography and detecting signals of VLDL, LDL and HDL in the separated lipoprotein particles; and
  calculating a value according to any one formula selected from (I) to (V):

$$Vs+Ls-Hs; \qquad (I)$$

$$Vs+Ls; \qquad (II)$$

$$Ls; \qquad (III)$$

$$(Vs+Ls)/Hs; \text{ and} \qquad (IV)$$

$$Ls/Hs, \qquad (V)$$

wherein: "Vs" represents the cholesterol content in small VLDL; "Ls" represents the sum of cholesterol contents in small LDL and very small LDL; and "Hs" represents the cholesterol content in large HDL.

13. The method of diagnosis according to claim 12, wherein said step of analyzing further comprises a step of comparing the calculated value with the reference value.

* * * * *